(12) United States Patent
Seong et al.

(10) Patent No.: US 10,953,086 B2
(45) Date of Patent: Mar. 23, 2021

(54) UNIVERSAL INFLUENZA VACCINE USING COLD-ADAPTED LIVE-ATTENUATED VIRUS

(71) Applicant: INDUSTRY-ACADEMIC COOPERATION FOUNDATION, YONSEI UNIVERSITY, Seoul (KR)

(72) Inventors: Baik Lin Seong, Seoul (KR); Yo Han Jang, Goyang-si (KR); Young Ho Byun, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 16/265,132

(22) Filed: Feb. 1, 2019

(65) Prior Publication Data
US 2019/0365882 A1    Dec. 5, 2019

(30) Foreign Application Priority Data
Jun. 1, 2018    (KR) .......................... 10-2018-0063500

(51) Int. Cl.
| | |
|---|---|
| *A61K 39/145* | (2006.01) |
| *A61K 49/00* | (2006.01) |
| *A61K 39/12* | (2006.01) |
| *C12N 9/24* | (2006.01) |
| *A61P 31/16* | (2006.01) |
| *C12N 15/52* | (2006.01) |

(52) U.S. Cl.
CPC ............ *A61K 39/145* (2013.01); *A61K 39/12* (2013.01); *A61K 49/00* (2013.01); *A61P 31/16* (2018.01); *C12N 9/2402* (2013.01); *C12N 15/52* (2013.01); *C12Y 302/01018* (2013.01)

(58) Field of Classification Search
None
See application file for complete search history.

(56) References Cited

U.S. PATENT DOCUMENTS 7,758,867 B2 *  7/2010  Seong ................... A61K 39/12
                                                          424/206.1
2011/0243987 A1 * 10/2011  Hanon .................. A61P 31/16
                                                          424/209.1

OTHER PUBLICATIONS

Seo et al., Immediate and broad-spectrum protection against heterologous and heterotypic lethal challenge in mice by live influenza vaccine, Vaccine, 2007, vol. 25, pp. 8067-8076.*
Jang et al., Protective efficacy in mice of monovalent and trivalent live attenuated influenza vaccines in the background of cold-adapted A/X-31 and B/Lee/40 donor strains, Vaccine, 2014, VOl. 32, pp. 535-543.*
Sanofi-Pasteur, Fluzone package insert, 2015.*
Jang et al., Immunogenicity and protective efficacy of cold-adapted X-31 liveattenuated pre-pandemic H5N1 influenza vaccines, Vaccine, 2013, vol. 31, pp. 3339-3346.*
Gen Bank Accession GQ132185, Influenza A virus (A/Korea/01/2009(H1N1)) segment 6 neuraminidase (NA) gene, complete cds, 2010.*
Gen Bank Accession GQ131023, Influenza A virus (A/Korea/01/2009(H1N1)) segment 4 hemagglutinin (HA) gene, complete cds, 2010.*
Jang et al., "Pan-Influenza A Protection by Prime-Boost Vaccination with Cold-Adapted Live-Attenuated Influenza Vaccine in a Mouse Model," *Frontiers in Immunology*, 2018, 9: Article 116, 17 pages.

* cited by examiner

*Primary Examiner* — Benjamin P Blumel
(74) *Attorney, Agent, or Firm* — Norton Rose Fulbright US LLP

(57) ABSTRACT

Disclosed is a universal influenza vaccine composition and corresponding methods comprising at least one attenuated live-attenuated influenza vaccine. The vaccine composition can exhibit a cross-protective effect against a wide range of influenza viruses and can ensure a strong protection efficacy, a wide range of protection, and safety. In addition, a vaccination method of heterologous live vaccines of the present invention induces various immunological effects so that cross-immunogenicity and cross-protective ability are remarkably increased, and thus is expected to be usefully utilized as a universal influenza prevention method. A person who has a basal immunity through infection with an influenza virus or vaccination with an influenza vaccine can be regarded as being in a state where primary vaccination has already been performed, single vaccination with a live vaccine induces an enhanced cross-immune response, and thus it is possible to expect a wide range of protective effects against various viruses.

Figure 1:
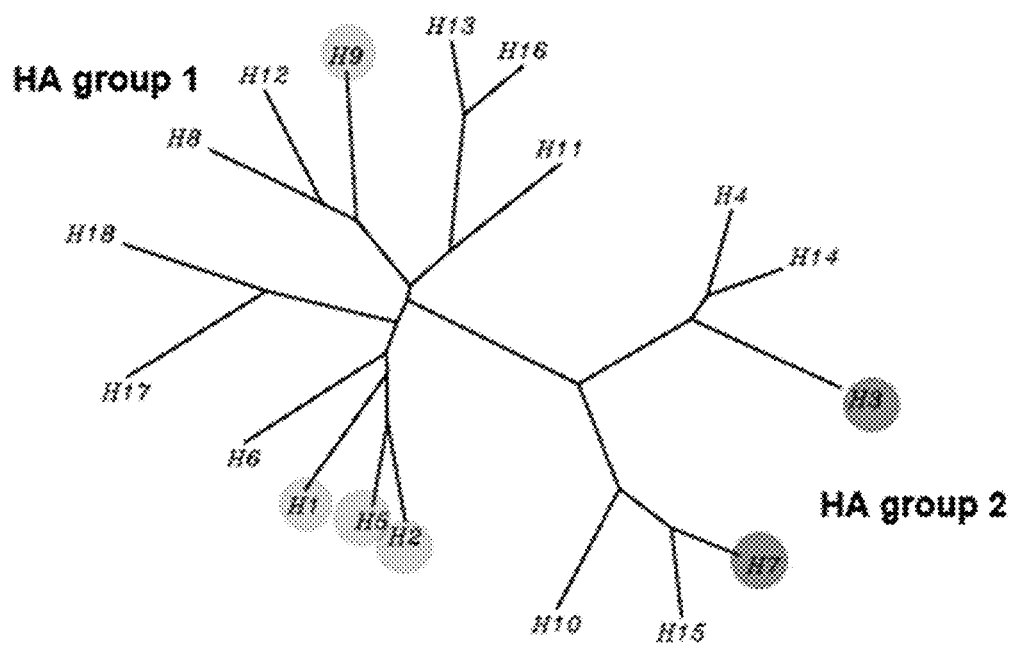
Figure 2A:
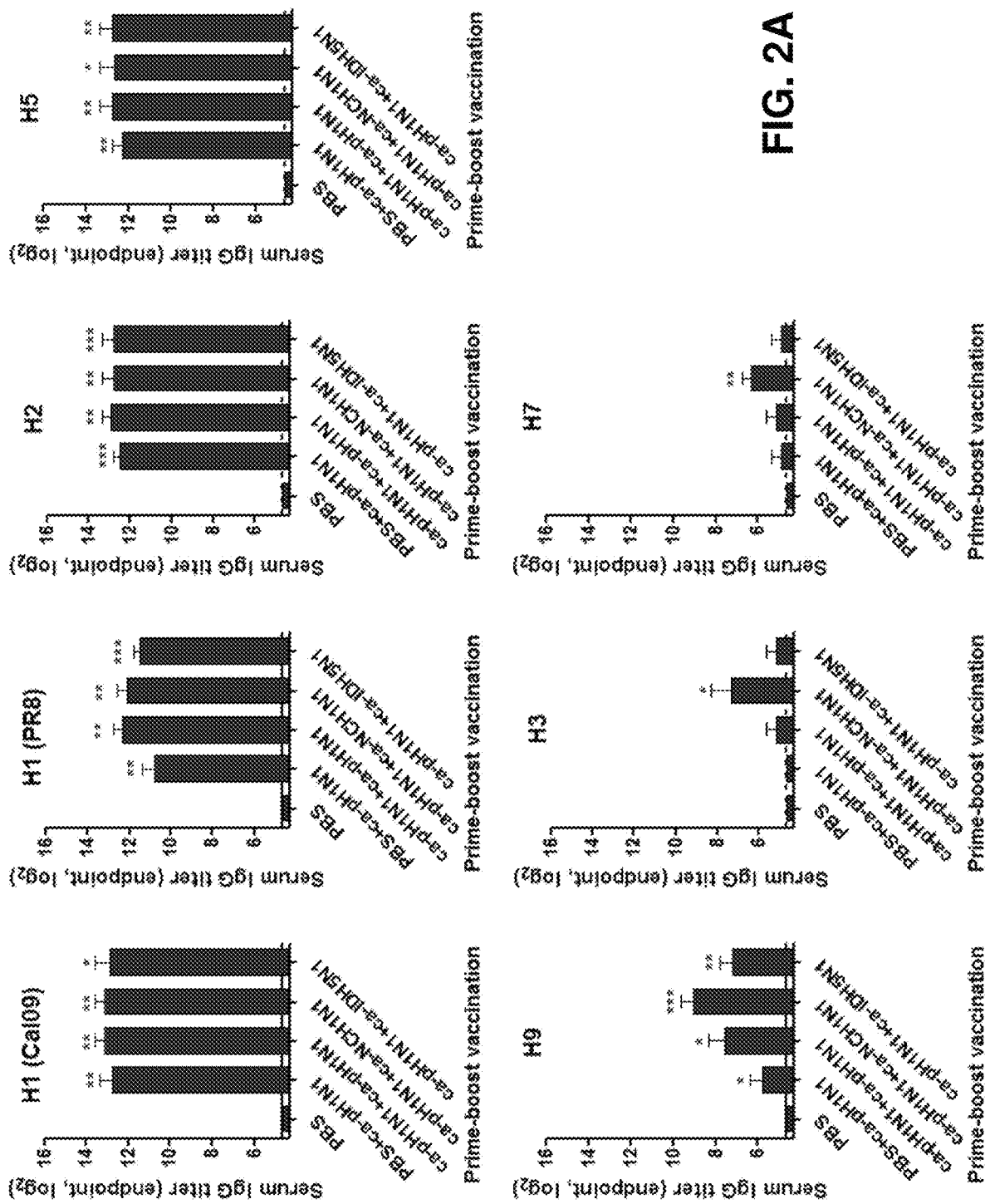
Figure 2B:
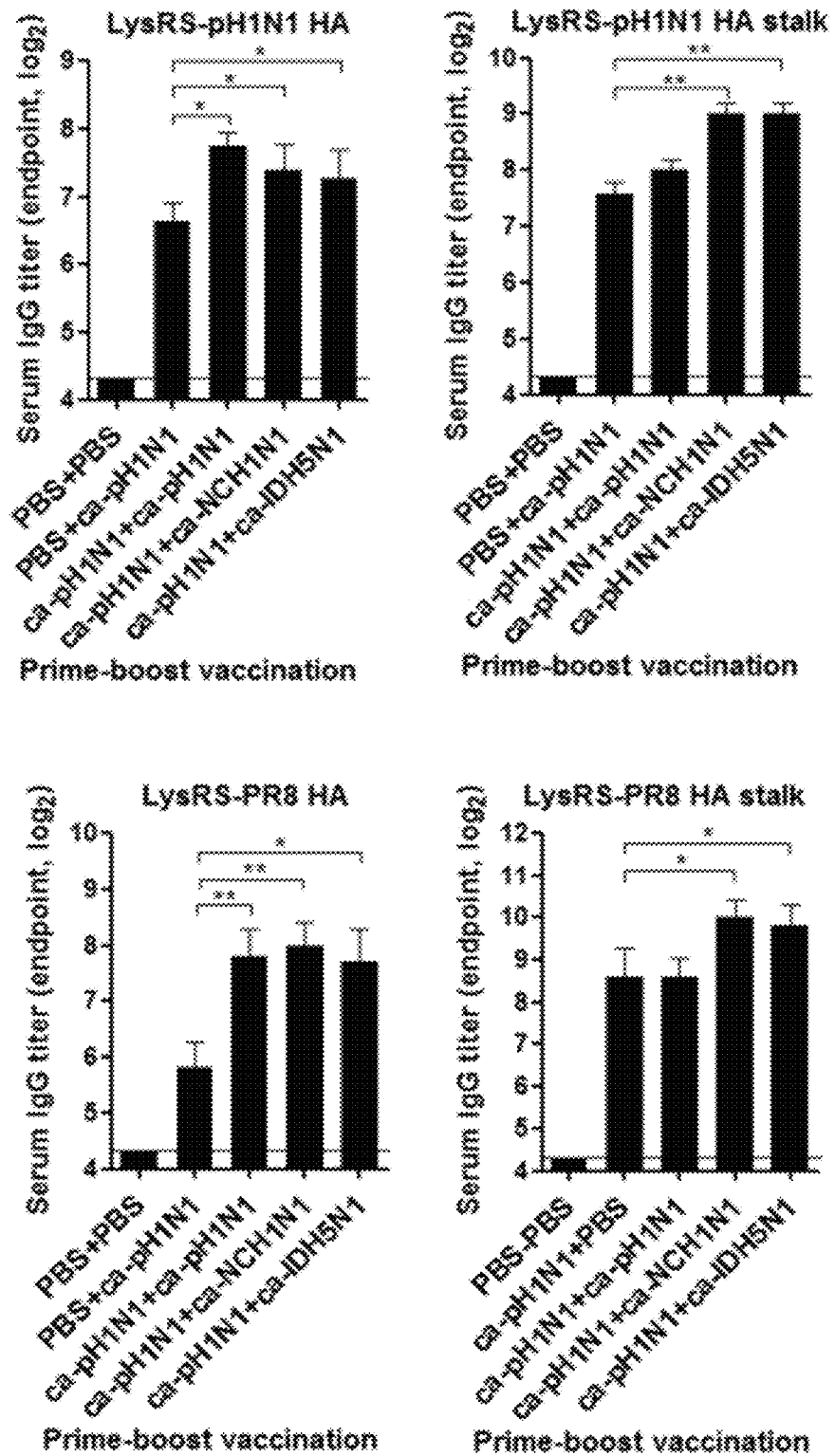
Figure 3:
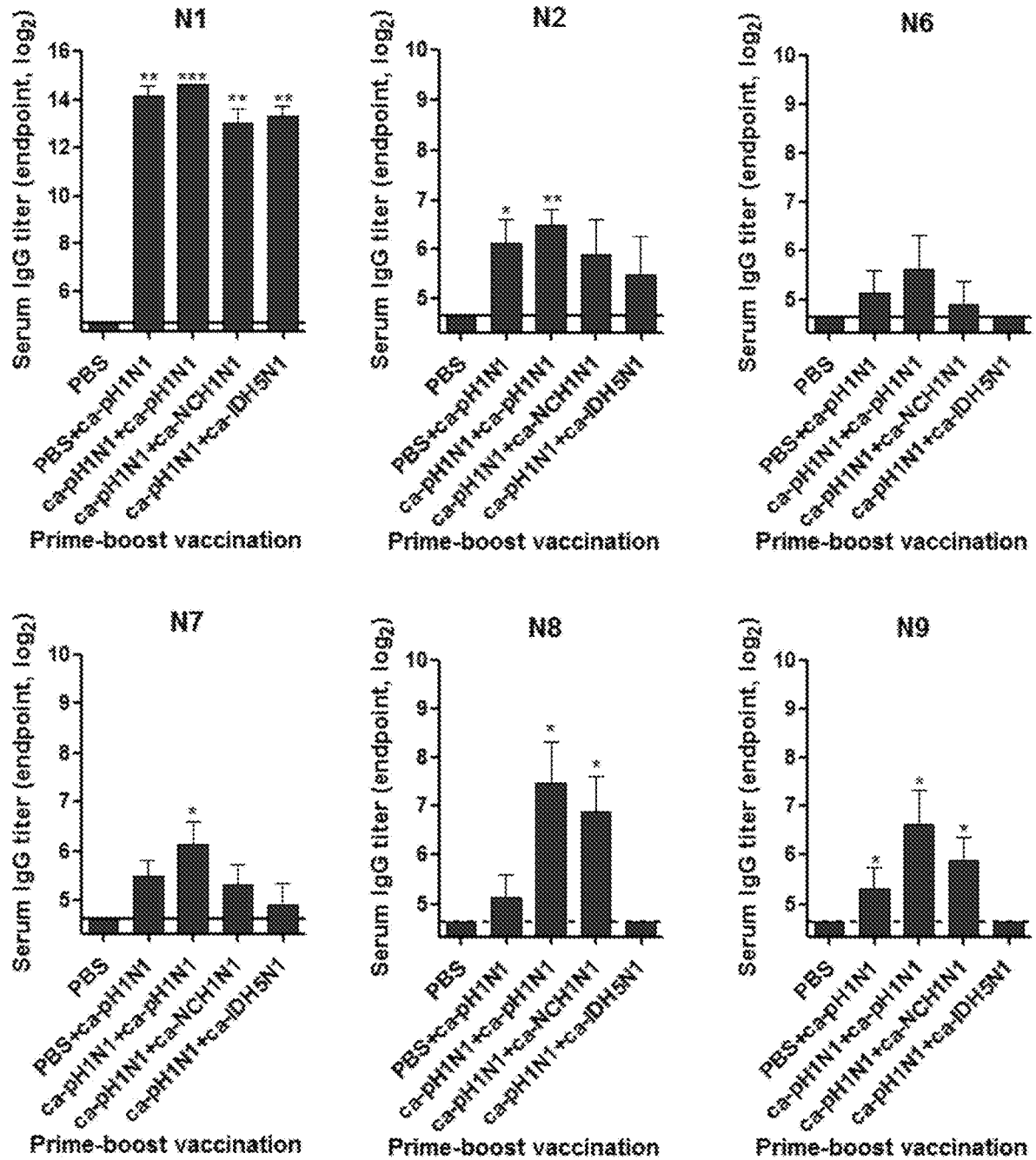
Figure 4A:
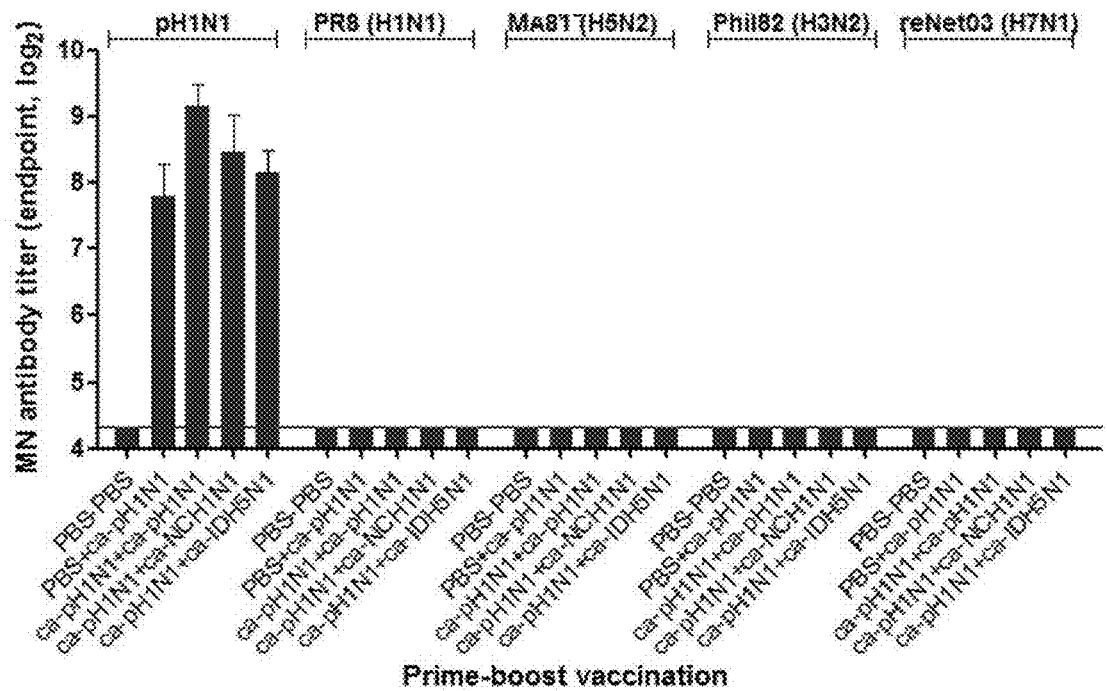
Figure 4B:
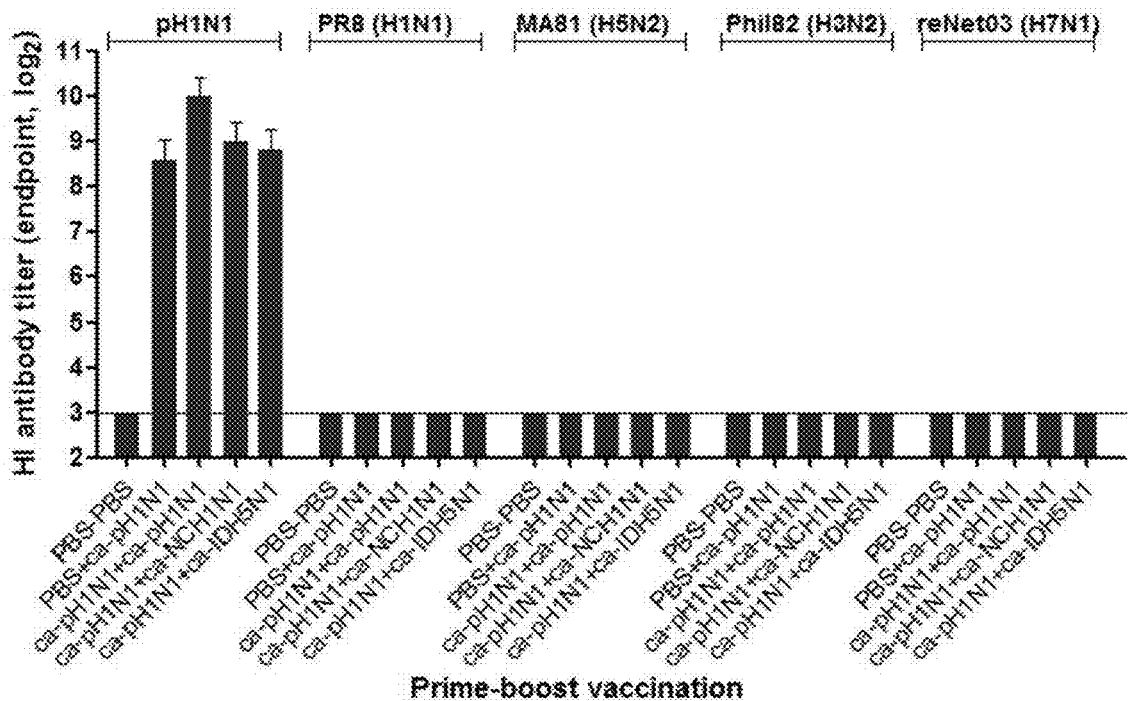
Figure 4C:
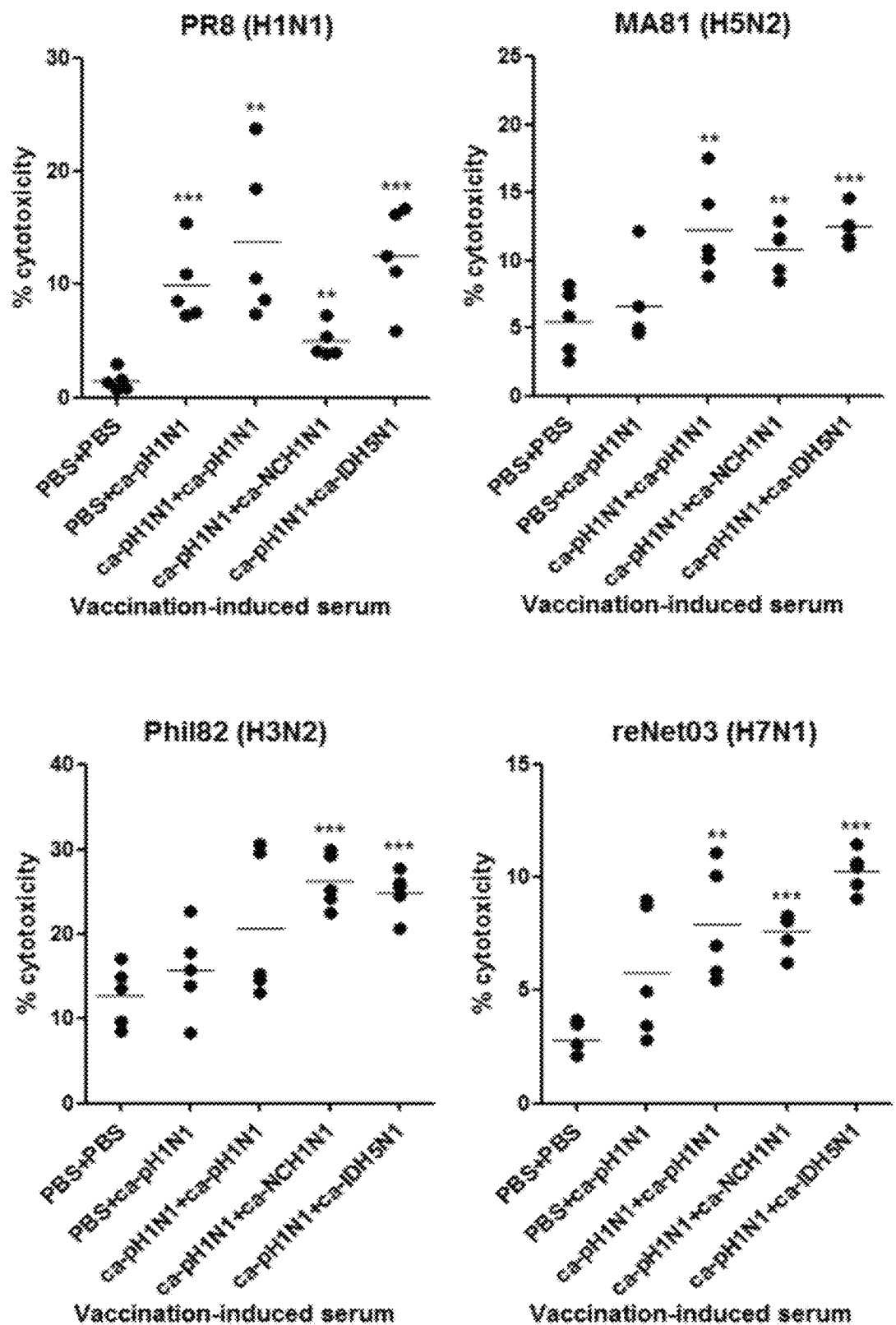

1 Claim, 16 Drawing Sheets
Specification includes a Sequence Listing.

UNIVERSAL INFLUENZA VACCINE USING COLD-ADAPTED LIVE-ATTENUATED VIRUS

CROSS-REFERENCE TO RELATED APPLICATIONS

This application claims priority to and the benefit of Korean Patent Application No. 10-2018-0063500, filed Jun. 1, 2018. The contents of the referenced patent application are incorporated into the present application by reference.

BACKGROUND

1. Field of the Invention

The present invention relates to a universal influenza vaccine using a cold-adapted attenuated virus. More particularly, the present invention relates to a universal influenza vaccine composition comprising at least one cold-adapted live-attenuated influenza vaccine and a vaccination method for influenza using the same.

2. Description of the Related Art

An influenza virus is an infectious respiratory pathogen that causes seasonal epidemics every year. In each season, 3 million to 5 million cases of severe illness and 250,000 to 500,000 deaths occur worldwide. Because of antigenic diversity and variability, an influenza vaccine has to be updated almost every year to match circulating strains. Currently used influenza vaccines provide strain-specific protection by primarily inducing neutralizing antibodies against hemagglutinin (HA) and neuraminidase (NA) which are surface glycoproteins of a virus.

Over the past several decades, efforts have been made to develop a universal influenza vaccine, via HA stalk-based methods, chimeric HA strategies, and the like.

Until now, the most advanced technology as a universal influenza vaccine technology is to provide cross-protection against influenza viruses of several HA subtypes by inducing antibodies to the stalk region which is a conserved region of the influenza viral HA. HA-stalk antibodies have neutralizing activity that eliminates infectivity of a virus by preventing structural changes of HA fusion peptide thus inhibiting a stage where the virus gene is delivered into the cytoplasm of a host cell. As representative two methods using the HA stalk, 1) a strategy of selectively inducing stalk antibodies by repeatedly inoculating chimeric HA proteins which are different in HA head region and are identical in stalk, and 2) a strategy of repeatedly inoculating stalk-only proteins which do not have a head region have been proposed.

However, the vaccine strategy based on the stalk antibodies showed many limitations in terms of protection efficacy, protection breadth, and safety. First, there are considerable amino acid sequence differences even in stalk region depending on HA subtypes (HA group 1 and HA group 2) in influenza A viruses. Due to this fact, most of the stalk vaccines exhibit a cross-protective ability only against viruses within the same HA group, and hardly exhibit a protective ability against viruses in the other HA group. Second, the stalk is less immunogenic than the head, and stalk antibodies have a weaker neutralizing ability than head antibodies. Thus, repeated vaccinations for 3 to 4 times are required to be able to provide an adequate level of protective ability. Third, it has been reported that stalk antibodies with non-neutralizing activity often fail to neutralize viruses and rather have a fatal adverse effect of increasing infectivity thereof. Finally, it has been experimentally demonstrated that mutant viruses showing resistance to stalk antibodies can occur.

As described above, an HA stalk-based vaccine has hurdles to overcome unsuitable for use as a universal vaccine in terms of protection efficacy, protection range, and safety. Nonetheless, the HA stalk-based vaccine has been recognized as the best method among the methods proposed so far and is in a clinical trial stage for humans.

Meanwhile, cold-adapted live-attenuated influenza vaccines (CAIVs) induces not only humoral immunity against viral surface antigen proteins but also cell-mediated immunity against internal proteins, and thus have an advantage of exhibiting an excellent cross-protective ability as compared with other vaccine platforms. However, despite such an excellent cross-protective ability, there is a problem of establishing quantitative protection correlates due to multi-layered and complicated immune responses, and moreover, live vaccines are not suitable for induction of stalk antibodies which are considered essential in development of universal vaccines. For these reasons, in development of universal vaccines, live vaccines have not received much attention. Therefore, if it is possible to enhance these advantages through appropriate methods, the live vaccine is expected to be a powerful platform for universal influenza vaccines.

However, up until now, regarding studies on live vaccines, there are only studies on development of vaccines targeting homologous strains, or cross-immunization studies for strains which are antigenically closely related. There is no known universal influenza vaccine using the live vaccine.

SUMMARY OF THE INVENTION

An object of the present invention is to provide a universal influenza live vaccine composition using a cold-adapted live-attenuated influenza vaccine.

Another object of the present invention is to provide a vaccination method for heterologous influenza viruses using the universal influenza live vaccine composition.

Still another object of the present invention is to provide a method for preventing or treating influenza, comprising administering a cold-adapted live-attenuated influenza vaccine to a subject.

However, the technical problem to be solved by the present invention is not limited to the above-mentioned problems, and other problems which are not mentioned can be clearly understood by those skilled in the art from the following description.

The present invention is intended to solve the above-mentioned problems, and provides a universal influenza live vaccine composition, comprising at least one influenza live vaccine that carries six internal genes represented by SEQ ID NOS: 1 to 6; influenza virus-derived surface hemagglutinin (HA) gene; and influenza virus-derived surface neuraminidase (NA) gene.

Specifically, the present invention provides a universal influenza live vaccine composition, comprising (a) a live vaccine composition for primary vaccination which contains an influenza live vaccine that carries six internal genes represented by SEQ ID NOS: 1 to 6; influenza virus-derived surface hemagglutinin (HA) gene; and influenza virus-derived surface neuraminidase (NA) gene; and (b) a live vaccine composition for secondary vaccination which contains an influenza live vaccine that carries six internal genes represented by SEQ ID NOS: 1 to 6; influenza virus-derived surface hemagglutinin (HA) gene; and influenza virus-derived surface neuraminidase (NA) gene.

The genes represented by SEQ ID NOS: 1 to 6 of the present invention are internal genes of X-31 ca virus, and are specifically PB2 (SEQ ID NO: 1), PB1 (SEQ ID NO: 2), PA (SEQ ID NO: 3), NP (SEQ ID NO: 4), M (SEQ ID NO: 5), and NS (SEQ ID NO: 6).

The universal influenza live vaccine composition of the present invention is for a prime-boost vaccination. The live vaccine composition for primary vaccination and the live vaccine composition for secondary vaccination are intended to be vaccinated respectively at a time interval, and the live vaccines may be the same or different in terms of composition.

The live vaccine for primary vaccination and the live vaccine for secondary vaccination carry the six internal genes of X-31 ca virus in common, and respectively carry any influenza virus-derived HA and NA gene sequences. The HA gene and the NA gene carried in one live vaccine may be HA gene and NA gene derived from the same influenza virus and may be a combination of HA gene and NA gene derived from different influenza viruses. In an embodiment of the present invention, the HA gene and NA gene derived from the same influenza virus were recombined in one live vaccine and used.

The live vaccine for primary vaccination and the live vaccine for secondary vaccination of the present invention may contain two or more viruses that carry HA and NA genes which are heterosubtypic to each other. As used herein, the term "heterosubtypic" means that the HA genes and the NA genes which constitute the live vaccine for primary vaccination and the live vaccine for secondary vaccination have different subtypes. In an embodiment of the present invention, ca-pH1N1 carrying A/Korea/1/09 (H1N1)-derived HA gene and NA gene was used as the live vaccine for primary vaccination, and ca-IDH5N1 carrying A/Indonesia/5/05 (H5N1)-derived HA gene and NA gene was used as the live vaccine for secondary vaccination. The live vaccine for primary vaccination and the live vaccine for secondary vaccination in the above-mentioned embodiment of the present invention are H1N1 and H5N1, respectively, and have different subtypes derived from different viruses. HA genes of influenza viruses are classified into group 1 and group 2. A combination of heterosubtypic live vaccines of the present invention may carry genes of viruses which are each derived from different HA groups, or may carry genes of viruses which belong to the same HA group but have different HA subtypes.

The live vaccine for primary vaccination and the live vaccine for secondary vaccination of the present invention may contain two or more viruses that carry HA and NA genes which are homosubtypic to each other. As used herein, the term "homosubtypic" means that the HA genes and the NA genes which constitute the live vaccine for primary vaccination and the live vaccine for secondary vaccination have the same subtype. In live vaccines having a homosubtypic relationship, respective HA genes and NA genes may be derived from the same virus or may be derived from different influenza viruses.

In an embodiment of the present invention, the live vaccine for primary vaccination and the live vaccine for secondary vaccination, which contain the homosubtypic viruses, may include influenza live vaccines which are homologous to each other. Here, the term "homologous" is intended to carry HA genes and NA genes derived from the same influenza virus, and means that the live vaccine for primary vaccination and the live vaccine for secondary vaccination are completely the same. These live vaccines can be used to administer the same live vaccine at a time interval. In an embodiment of the present invention, a primary vaccination and a secondary vaccination were performed using ca-pH1N1 that carries A/Korea/1/09 (H1N1)-derived HA gene and NA gene.

In an embodiment of the present invention, the live vaccine for primary vaccination and the live vaccine for secondary vaccination may include influenza live vaccines which are heterologous to each other. Here, the term "heterologous" is intended to carry HA genes and NA genes which are derived from different viruses, and may be homosubtypic or heterosubtypic depending on whether HA and NA subtypes of different viruses are identical. In an embodiment of the present invention, ca-pH1N1 carrying A/Korea/1/09 (H1N1)-derived HA gene and NA gene was used as the live vaccine for primary vaccination, and ca-NVH1N1 carrying A/New Caledonia/20/99 (H1N1)-derived HA gene and NA gene was used as the live vaccine for secondary vaccination. In this case, the live vaccine for primary vaccination and the live vaccine for secondary vaccination are derived from different viruses and are heterologous vaccines. At the same time, the live vaccines belong to homosubtypic vaccines due to having the same HA and NA gene subtypes.

The HA gene or the NA gene of the present invention may be derived from at least one influenza virus strain selected from the group consisting of A/Korea/1/09 (H1N1), A/New Caledonia/20/99 (H1N1), and A/Indonesia/5/05 (H5N1).

The HA gene of the present invention may include at least one selected from the group consisting of SEQ ID NO: 7, SEQ ID NO: 9, and SEQ ID NO: 11, in which SEQ ID NO: 7 represents a sequence of A/Korea/1/09 (H1N1)-derived HA gene, SEQ ID NO: 9 represents a sequence of A/New Caledonia/20/99 (H1N1)-derived HA gene, and SEQ ID NO: 11 represents a sequence of A/Indonesia/5/05 (H5N1)-derived HA gene.

The NA gene of the present invention may include at least one selected from the group consisting of SEQ ID NO: 8, SEQ ID NO: 10, and SEQ ID NO: 12, in which SEQ ID NO: 8 represents a sequence of A/Korea/1/09 (H1N1)-derived NA gene, SEQ ID NO: 10 represents a sequence of A/New Caledonia/20/99 (H1N1)-derived NA gene, and SEQ ID NO: 12 represents a sequence of A/Indonesia/5/05 (H5N1)-derived NA gene.

In an embodiment of the present invention, the live vaccine composition for primary vaccination or the live vaccine composition for secondary vaccination may contain at least one selected from the group consisting of i) an influenza live vaccine (ca-pH1N1) carrying A/Korea/1/09 (H1N1)-derived surface HA gene and surface NA gene; ii) an influenza live vaccine (ca-NCH1N1) carrying A/New Caledonia/20/99 (H1N1)-derived surface HA gene and surface NA gene; and (iii) an influenza live vaccine (ca-IDH5N1) carrying A/Indonesia/5/05 (H5N1)-derived surface HA gene and surface NA gene.

The influenza live vaccine of the present invention may exhibit a cold-adapted attenuated trait. The meaning of the terms "cold-adapted" and "attenuated" as used herein is known in the art. By "cold-adapted" is meant that a virus exhibits growth of 100-fold or lower at 33° C. as compared with its growth at 37° C. By "attenuated" is meant that a virus replicates in the mouse's upper airway but is not detectable in lung tissue, and does not cause influenza-type diseases in animals.

The universal influenza live vaccine composition of the present invention can produce a cross-immune response against HA proteins of different subtypes.

In an embodiment of the present invention, the composition may produce a cross-immune response against at least one HA protein (HA group 1) selected from the group consisting of H1, H2, H5, H6, H8, H9, H11, H12, H13, and H16; and at least one HA protein (HA group 2) selected from the group consisting of H3, H4, H7, H10, H14, and H15.

In addition, in another embodiment of the present invention, the composition may produce a cross-immune response against HA proteins of two or more different subtypes which belong to HA group 1, and against HA proteins of two or more different subtypes which belong to HA group 2.

The universal influenza live vaccine composition of the present invention can produce a cross-immune response against NA proteins of different subtypes.

The present invention also provides a vaccination method for heterologous influenza viruses, comprising administering two times or more, to an animal, an influenza live vaccine that carries six internal genes represented by SEQ ID NOS: 1 to 6; influenza virus-derived surface hemagglutinin (HA) gene; and influenza virus-derived surface neuraminidase (NA) gene.

In an embodiment of the present invention, the HA gene of the influenza live vaccine may be selected from the group consisting of SEQ ID NO: 7, SEQ ID NO: 9, and SEQ ID NO: 11, and the NA gene may be selected from the group consisting of SEQ ID NO: 8, SEQ ID NO: 10, and SEQ ID NO: 12.

In an embodiment of the present invention, the influenza live vaccine used in the vaccination method may be selected from the group consisting of i) an influenza live vaccine (ca-pH1N1) carrying A/Korea/1/09 (H1N1)-derived surface HA gene and surface NA gene; ii) an influenza live vaccine (ca-NCH1N1) carrying A/New Caledonia/20/99 (H1N1)-derived surface HA gene and surface NA gene; and (iii) an influenza live vaccine (ca-IDH5N1) carrying A/Indonesia/5/05 (H5N1)-derived surface HA gene and surface NA gene.

In an embodiment of the invention, the administering may include a prime-boost vaccination.

The meaning of the term "prime-boost vaccination" as used herein is known in the art and is a vaccination method which comprises a step of performing prime vaccination (primary vaccination) of an immunogenic composition or vaccine, and a step of performing booster vaccination (secondary vaccination) at a certain time interval from the prime vaccination. The immunogenic composition or vaccine used for prime vaccination may be the same as or different from that used for booster vaccination. The time interval between prime vaccination and booster vaccination varies depending on the kind and body weight of an individual to be vaccinated, and the type and amount of a vaccine to be vaccinated. There is no limitation on the time interval.

In an embodiment of the present invention, the prime-boost vaccination may include administering (a) a live vaccine composition for primary vaccination which contains an influenza live vaccine that carries six internal genes represented by SEQ ID NOS: 1 to 6; influenza virus-derived surface hemagglutinin (HA) gene; and influenza virus-derived surface neuraminidase (NA) gene; and administering (b) a live vaccine composition for secondary vaccination which contains an influenza live vaccine that carries six internal genes represented by SEQ ID NOS: 1 to 6; influenza virus-derived surface hemagglutinin (HA) gene; and influenza virus-derived surface neuraminidase (NA) gene.

In an embodiment of the present invention, the prime-boost vaccination may include administering a live vaccine composition for primary vaccination which contains an influenza live vaccine selected from the group consisting of i) an influenza live vaccine (ca-pH1N1) carrying A/Korea/1/09 (H1N1)-derived surface HA gene and surface NA gene; ii) an influenza live vaccine (ca-NCH1N1) carrying A/New Caledonia/20/99 (H1N1)-derived surface HA gene and surface NA gene; and (iii) an influenza live vaccine (ca-IDH5N1) carrying A/Indonesia/5/05 (H5N1)-derived surface HA gene and surface NA gene; and administering a live vaccine composition for secondary vaccination which contains an influenza live vaccine selected from the above group. The first influenza live vaccine and the second influenza live vaccine may be the same or different.

In an embodiment of the present invention, the vaccination method may be such that the live vaccine compositions are administered to an animal other than a human.

The present invention also provides a method for preventing or treating influenza, comprising administering, to a subject, a first live vaccine composition that carries six internal genes represented by SEQ ID NOS: 1 to 6; influenza virus-derived surface hemagglutinin (HA) gene; and influenza virus-derived surface neuraminidase (NA) gene; and administering, to the subject, a second live vaccine composition that carries six internal genes represented by SEQ ID NOS: 1 to 6; influenza virus-derived surface hemagglutinin (HA) gene; and influenza virus-derived surface neuraminidase (NA) gene.

The present inventors have completed the present invention by experimentally proving that a prime-boost vaccination using an influenza live vaccine strain promotes immunity, and thus exhibits a strong and broad cross-immune effect.

Major human infective influenza A viruses, H1N1, H3N2, H5N1, H7N1, and the like, include all viruses belonging to HA group 1 and HA group 2. In order to develop an effective universal influenza vaccine, it is required to provide a cross-immune effect on viruses belonging to HA group 1 and HA group 2. This technology is a strategy to provide protection against all viruses belonging to HA group 1 and HA group 2 using a live vaccine, and it has been experimentally identified that it is possible to provide protection against a whole range of influenza A viruses which could not be achieved with HA-based universal vaccine strategies developed so far.

Specifically, according to an embodiment of the present invention, a prime-boost vaccination was performed using x-31 ca-based cold-adapted live-attenuated influenza vaccines of different strains. Experimental mice were vaccinated with live vaccines of different prime-boost combinations, and cross-preventive effects against antigenically different HA group 1 influenza viruses (H1 and H5) and HA group 2 influenza viruses (H3 and H7) were checked. As a result, complete protection against the group 1 viruses (H1N1, H5N2) and the group 2 viruses (H3N2, H7N1) was achieved through a double vaccination with H1N1 and H5N1 influenza live vaccines. In addition, despite challenge of high mortality (10 $MLD_{50}$), a perfect level of cross-protective effect was exhibited with no weight loss at all in mice. Furthermore, non-neutralizing antibodies induced by vaccination show ADCC activity while not causing any adverse effects such as increased infectivity of virus or immune interference between the live vaccines. That is, it can be said that vaccination of the present invention has an excellent advantage over conventional HA stalk-based vaccines in terms of protection efficacy and safety as well as protection range.

The universal influenza live vaccine composition of the present invention can be expected to have a strong protection efficacy, a wide protection range, and a safe preventive effect, which could not be expected in conventional HA vaccines, by being vaccinated with a prime-boost method. In addition, the vaccination method of heterologous live vaccines of the present invention induces various immunological effects so that cross-immunogenicity and cross-protective ability are remarkably increased, and thus is expected to be usefully utilized as a universal influenza prevention method.

In addition, according to the vaccination method of live vaccines of the present invention, since a person who has a basal immunity through infection with an influenza virus or vaccination with an influenza vaccine can be regarded as being in a state where primary vaccination has already been performed, single vaccination with a live vaccine (which corresponds to a booster vaccination) induces an enhanced cross-immune response, and thus it is possible to expect a wide range of protective effects against various viruses.

BRIEF DESCRIPTION OF THE DRAWINGS

FIG. 1 (A) illustrates a prime-boost live vaccine combination for each vaccination experiment group; (B) illustrates a phylogenetic classification diagram for influenza virus HA subtypes.

FIG. 2A illustrates the results obtained by analyzing a cross-linking ability of vaccine-induced antibodies against HA proteins (n=5, mean±standard deviation, significance in a case where a comparison is made between a vaccinated group and a PBS control group: *, P<0.001, P<0.01; *, P<0.05).

FIG. 2B illustrates the results obtained by analyzing cross-linking ability of vaccine-induced antibodies against HA whole proteins or HA stalk regions (n=5, mean±standard deviation, significance in a case where a comparison is made between two different vaccinated groups: *, P<0.001; , P<0.01; *, P<0.05).

FIG. 3 illustrates the results obtained by analyzing a cross-linking ability of vaccine-induced antibodies against NA proteins (n=5, mean±standard deviation, significance in a case where a comparison is made between a vaccinated group and a PBS control group: *, P<0.001; , P<0.01; *, P<0.05).

FIG. 4A illustrates the results of microneutralization assay (MN assay) of vaccine-induced antibodies (n=5, mean±standard deviation, significance in a case where a comparison is made between a vaccinated group and a PBS control group: *, P<0.001; , P<0.01; *, P<0.05).

FIG. 4B illustrates the results of hemagglutinin inhibition assay (HI assay) of vaccine-induced antibodies (n=5, mean±standard deviation, significance in a case where a comparison is made between a vaccinated group and a PBS control group: *, P<0.001; , P<0.01; *, P<0.05).

FIG. 4C illustrates the results obtained by measuring antibody-dependent cell-mediated cytotoxicity (ADCC) activity of vaccine-induced antibodies (n=5, mean±standard deviation, significance in a case where a comparison is made between a vaccinated group and a PBS control group: *, P<0.001; , P<0.01; *, P<0.05).

FIG. 5 illustrates the results obtained by identifying cross-protective ability against challenge with heterologous influenza viruses by weight loss and mortality for each vaccinated group in mice (A, non-inoculated control group, B to E, live vaccine-inoculated groups, n=4).

FIG. 6 illustrates the maximum loss in mouse weight following challenge with heterologous influenza viruses for each vaccinated group in mice.

FIG. 7 illustrates lung tissue viral growth inhibition following challenge with heterologous influenza viruses for each vaccinated group in mice (n=5, mean±standard deviation, significance in a case where a comparison is made between two different vaccinated groups: *, P<0.001; , P<0.01; *, P<0.05).

FIG. 8 illustrates the results of assay for memory CTL activity after infection with viruses (n=3 to 5, mean±standard deviation, significance in a case where a comparison is made between control groups (D, E) or two different vaccinated groups (F): **, P<0.01; *, P<0.05).

FIG. 9A illustrates an outline of an assay experiment for cross-protective contribution of T cells and NK cells in vaccinated mice.

FIGS. 9B to 9F illustrate the results obtained by identifying weight change and survival rate of mice in non-vaccinated (B) and vaccinated (C to F) experimental groups.

FIGS. 10A and 10B illustrate the results obtained by identifying whether non-neutralizing antibodies cause a phenomenon of increased infectivity of heterologous influenza viruses in MDCK cells (A) and RAW264.7 cells (B).

FIG. 10C illustrates the results obtained by identifying whether an immune interference effect between heterologous live vaccines causes a phenomenon of inhibited antibody response.

DETAILED DESCRIPTION OF EXEMPLARY EMBODIMENTS

Hereinafter, the present invention will be described in more detail by way of examples. These examples are intended to merely illustrate the present invention, and it will be apparent to those skilled in the art that the scope of the present invention is not construed as being limited by these examples.

[Experimental Materials and Methods]

1. Cell Lines

Madin-Darby canine kidney (MDCK) cells (ATCC CCL-34) were cultured in minimum essential medium (MEM) (HyClone) supplemented with 10% fetal bovine serum (FBS) (HyClone). Mouse macrophage cell line RAW 264.7 (ATCC TIB-71) was cultured in Dulbecco's Modified Eagle Medium (DMEM) (HyClone) supplemented with 10% FBS.

2. Vaccines and Viruses

The X-31 ca-based live vaccines (CAIVs) of the present invention are reassortant viruses which carry six internal genes of X-31 ca donor strain in common, and carry surface HA and NA genes of A/Korea/1/09 (H1N1) (GQ131023 and GQ132185), A/New Caledonia/20/99 (H1N1) (CY031336 and CY033624), or A/Indonesia/5/05 (H5N1) (CY116646 and CY116648). The X-31 ca is a reassortant virus which is obtained by cold-adapting parental X-31 virus strain and carries the HA and NA genes of A/Hong Kong/1/1968 (H3N2) in A/Puerto Rico/8/34 (H1N1). The genetic information (GenBank database accession numbers) of the six internal genes of X-31ca is as follows: DQ874873 (PB2, SEQ ID NO: 1), DQ874874 (PB1, SEQ ID NO: 2), DQ874875 (PA, SEQ ID NO: 3), DQ874877 (NP, SEQ ID NO: 4), DQ874879 (M, SEQ ID NO: 5), and DQ874880 (NS, SEQ ID NO: 6). Attenuated phenotype, vaccine efficiency, and safety for all live vaccines have been established in animal models through previous studies.

Experimental viruses used in the examples of the present invention include two laboratory strains (PR8 (H1N1) (A/Puerto Rico/8/34) and MA81 (H5N2) (A/aquatic bird/Korea/w81/05)), one wild type virus (Phil82 (H3N2)

(A/Philippines/2/82)), and one 7:1 reassortant virus (re-Net03 (H7N1) (PR8:HA of A/Netherlands/219/03)).

Mouse lethal dose 50 (MLD$_{50}$) of each virus was determined by a preliminary experiment; and PR8 (H1N1) is $5\times10^3$ plaque forming unit (PFU), MA81 (H5N2) is $1\times10^4$ PFU, Phil82 (H3N2) is $5\times10^4$ PFU, and reNet03 (H7N1) is $5\times10^3$ PFU.

3. Recombinant Influenza HA Proteins

HA proteins expressed in insect cells were purchased from Sino Biological Inc. (China). The seven different HA proteins were derived from A/California/6/2009 (H1N1), A/Puerto Rico/8/1934 (H1N1), A/Canada/720/2006 (H2N2), A/Indonesia/5/2005 (H5N1), A/Hong Kong/35820/2009 (H9N2), A/Sydney/5/1997 (H3N2), and A/Anhui/1/2013 (H7N9) influenza viruses, respectively.

The present inventors also expressed the HA proteins using a bacterial expression system. Specifically, the HA protein without transmembrane domain (HAΔTM) (positions 1 to 531 in H1 numbering) and the stalk region (positions 345 to 531 in H1 numbering) in the HA2 domain of PR8 (H1N1) and A/Korea/1/09 (H1N1) viruses were expressed in *Escherichia coli*. The transmembrane domain (positions 532 to 566) was removed for soluble expression of the HAΔTM protein. The expression plasmid (pLysRS-GE) was transformed into *Escherichia coli* BL21(DE3) pLysS, and the proteins were expressed. Next, the cell lysates were centrifuged and separated into the soluble fraction and insoluble fraction. Then, the resultant was subjected to SDS-PAGE, and identified by staining with Coomassie brilliant blue R-250. The expressed proteins were purified using nickel affinity chromatography.

4. Mouse Live Vaccine Inoculation and Challenge

6-Week-old balb/c female mice were used for mouse vaccination experiments, and a total of five prime-boost vaccination experimental groups were constructed using three live vaccines, ca-pH1N1 (2009 pandemic influenza A/Korea/1/09 (H1N1) virus), ca-NCH1N1 (seasonal influenza A/New Caledonia/20/99 (H1N1) virus), and ca-IDH5N1 (highly-pathogenic H5N1 avian influenza A/Indonesia/5/05 (H5N1) virus). The prime-boost combination for each experimental group is shown in FIG. 1A.

Nasal administration of $10^5$ PFU of live vaccine was carried out for each experimental group, and primary vaccination (prime) and secondary vaccination (boost) were performed at a 2-week interval. Four weeks after the secondary vaccination, challenge with $10\times$MLD$_{50}$ of viruses was performed. The viruses for challenge include two viruses (H1N1, H5N2) belonging to HA group 1 and two viruses (H3N2, H7N1) belonging to HA group 2.

The phylogenetic classification diagram for influenza virus HA subtypes is shown in FIG. 1B. HAs, which are included in tests for vaccine's protective ability and binding ability with vaccine-induced antibodies in the present invention, are highlighted in colors. The three live vaccines used in the present invention equally carry six internal genes derived from X-31 ca, and carry different surface genes from other viruses (H1, H5) which each belong to HA group 1. On the other hand, the viruses for challenge were designed by including both HA strains of two groups. These experimental designs allow for evaluation of protection efficacy and protection range against various influenza viruses belonging to influenza A HA groups 1 and 2.

Example 1. Assay for Cross-Reactive Binding Ability of Vaccine-Induced Antibodies to HA Proteins Due to the fact that HA proteins act as major immune antigens in preventing influenza virus infection, in order to identify a binding ability of the vaccine-induced serum IgG antibodies of the present invention to heterologous influenza virus HA proteins, ELISA experiments were carried out using, as coating antigens, recombinant HA proteins of seven subtypes of influenza viruses expressed in insect cells. The HA proteins used in the experiments were derived from five HAs (A/California/6/2009 (H1N1), A/Puerto Rico/8/1934 (H1N1), A/Canada/720/2006 (H2N2), A/Indonesia/5/2005 (H5N1), and A/Hong Kong/35820/2009 (H9N2)) belonging to group 1 and two HAs (A/Sydney/5/1997 (H3N2) and A/Anhui/1/2013 (H7N9)) belonging to group 2.

96-Well plates were coated overnight with 100 μl of $10^5$ PFU of sucrose-gradient purified virus or 1 μg/ml of the HA protein. After performing blocking with 150 μl of 1% BSA in PBS and washing the plates, the wells were incubated with 100 μl of 2-fold serially diluted sera or BALF for 1 hour at room temperature. After washing the plates, the wells were incubated with 100 μl of HRP-conjugated secondary goat anti-mouse IgG antibody or IgA antibody at room temperature for 1 hour. Next, the plates were washed and supplemented with 100 μl of TMB solution. Then, the plates were allowed to react for 30 minutes at room temperature in the dark. The reaction was stopped by adding 50 μl of 2 N H2504 solution, and then $OD_{450}$ was measured on an ELISA reader. Antibody titers were calculated as the endpoint dilution that yields an OD value greater than the mean+2 SD of the control group.

As a result, as shown in FIG. 2A, in a case of the HA proteins belonging to group 1, all vaccine-induced antibodies exhibited a very high level of binding ability with an antibody titer of 1,760 to 9,000 to the H1, H2, and H5 HA proteins, which are antigenically close to the vaccine strain. For the H9 HA protein, which is relatively antigenically distant from the vaccine strain, double vaccination elicited an antibody titer which is 3- to 10-fold increased over single vaccination. In addition, even for the H3 and H7 HA proteins, which belong to group 2 and are different from the vaccine strain, a significant binding ability with an antibody titer of 25 to 160 was exhibited.

The serum antibodies induced by vaccination with live vaccines of the present invention exhibited a broad binding ability covering both HA groups 1 and 2. In particular, for the H9, H3, and H7 HAs, the highest antibody titer was exhibited in the ca-pH1N1+ca-NCH1N1 vaccinated sera. From this, for the HAs which are antigenically distant, it was found that a cross-linking ability of the antibodies may vary depending on a prime-boost combination.

Next, in order to analyze a binding ability of the vaccine-induced serum IgG antibodies to the whole HA protein and stalk region, ELISA was performed using the whole HA proteins and stalk regions which had been expressed in *Escherichia coli* and are derived from A/Korea/1/09 (pH1N1) and PR8 (H1N1) viruses.

As a result, as shown in FIG. 2B, for the pH1N1 HA, double vaccination with live vaccines exhibited 1.5- to 2-fold increased antibody titer over single vaccination with a live vaccine. For the pH1N1 HA stalk, a remarkable increase of antibody titer from 192 in the single vaccination to 250 to 520 in the double vaccination was exhibited. For the PR8 HA, the double vaccination exhibited about 4-fold increase in antibody titer over the single vaccination. For the PR8 HA stalk, in a case of being additionally vaccinated with a live vaccine strain which is homologous to that used in the single vaccination, almost the same antibody titer was exhibited; and in a case of being additionally vaccinated with a heterologous live vaccine strain, a 2-fold or more increased antibody titer was exhibited. From this, it was found that in order to induce HA stalk antibodies, the double vaccination with heterologous live vaccines is more effective than the double vaccination with homologous live vaccines.

These results suggest that immunologically dominant HA head antibodies are increased at the time of double vaccination with homologous live vaccines, while antibodies to HA stalk regions that are conserved between different viruses can be selectively induced at the time of double vaccination with heterologous live vaccines of different HAs.

Example 2. Assay for Cross-Linking Ability of Vaccine-Induced Antibodies to NA Proteins In order to analyze a binding ability of the vaccine-induced serum IgG antibodies to NAs, ELISA was carried out using, as coating antigens, NA proteins of six subtypes expressed in insect cells. The NA proteins used in the experiments were derived from A/California/04/2009 (H1N1), A/Aichi/2/1968 (H3N2), A/mallard/Ohio/657/2002 (H4N6), A/Netherlands/219/2003 (H7N7), A/duck/Guangdong/E1/2012 (H10N8), and A/Anhui/1/2013 (H7N9).

As a result, as shown in FIG. 3, for the N1 protein which is of the same subtype as the vaccine strain, the antibodies exhibited a high level of binding ability with an antibody titer of 8,320 to 25,600 in all vaccine-induced sera. For the N6 NA, no significant antibody titer was measured. However, for the N2, N7, N8, and N9 NAs, a significant antibody binding ability with an antibody titer of 30 to 180 was exhibited in some vaccine-induced sera. In particular, for all NAs, the highest antibody binding ability was exhibited at the time of double vaccination with homologous live vaccines. Such results were different from those for the HA protein in Example 1 above. From this, it was found that vaccination with live vaccines elicits an antibody response with cross-reactivity to various NA subtypes.

Example 3. Analysis for Cross-Protective Ability Mediated by Vaccine-Induced Antibodies 3-1. Assay for Activity of Serum Antibodies to Neutralize Virus In order to evaluate virus neutralizing activity of the vaccine-induced antibodies, microneutralization assay (MN assay) and hemagglutinin inhibition assay (HI assay) were performed to measure neutralizing antibody titers.

Specifically, for the MN assay, sera were pre-treated with a receptor-destroying enzyme, incubated overnight at 37° C., and then inactivated at 56° C. for 30 minutes. Next, 50 μl of 2-fold serially diluted sera was mixed with 100 tissue cell infectious dose 50 ($TCID_{50}$) of viruses. The mixtures were added to MDCK cells grown in a 96-well plate so as to cause infection. Viral infection was identified by a cytopathic effect (CPE), and the MN antibody titer was calculated as the highest diluted concentration that completely suppresses CPE.

For the HI assay, in the same manner as above, sera were pre-treated with a receptor-destroying enzyme, incubated overnight at 37° C., and then inactivated at 56° C. for 30 minutes. Next, 25 μl of 2-fold serially diluted sera was incubated with the same volume of 4 HA units of four heterologous influenza viruses at 37° C. for 1 hour. Then, 50 μl of 1% chicken red blood cells was added thereto and incubation was performed at 4° C. for 1 hour. HI antibody titer was calculated according to the highest dilution factor that completely suppresses hemagglutination.

As a result, as shown in FIGS. 4A and 4B, neutralizing antibody titers were measured only for pH1N1 which is a virus homologous to the vaccine strain. For the four heterologous influenza viruses, no MN or HI antibody titers were measured.

3-2. Measurement of Antibody-Dependent Cell-Mediated Cytotoxicity (ADCC) Activity of Serum Antibodies ADCC assay was performed to identify whether vaccine-induced serum antibodies exhibit antibody-dependent cell-mediated cytotoxicity (ADCC) against virus-infected MDCK cells. Primary spleen cells extracted from mice were used instead of natural killer (NK) cells.

Confluent MDCK cells grown in 96-well plates were infected with each of four influenza viruses, and incubated in a MEM medium which is supplemented with 20 μM of Z-VAD-FMK (Promega) and pan-caspase inhibitor, and in which trypsin is excluded. Eight hours after the infection, the supernatant was removed and 100 μl of sera (1:10 dilution) was added to the MDCK cells and then incubated for 1 hour at 37° C. Next, 100 μl of mouse spleen cells ($10^6$ cells) pre-treated with RBC lysis buffer was added to each well and incubated for 2 hours at 37° C. Cytotoxicity of target MDCK cells was calculated by measuring an amount of lactate dehydrogenase (LDH) proteins which had leaked out of the cells due to MDCK cell death.

As a result, as shown in FIG. 4C, all vaccine sera exhibited ADCC activity to kill PR8 virus-infected cells, and some vaccine sera exhibited significant ADCC activity against H5N2, H3N2, and H7N1 virus-infected cells.

From this, it was found that although the vaccine-induced antibodies do not have the activity of directly neutralizing heterologous influenza viruses, such antibodies contribute to cross-protection through the ADCC activity capable of removing virus-infected cells. Assay for ADCC activity of live vaccine-induced antibodies shows new results which have not been identified in the previous study (JVI, 2012), indicating that non-neutralizing antibodies induced by live vaccines can remove heterologous influenza virus-infected cells through ADCC activity.

Example 4. Cross-Protective Ability Against Challenge with Heterologous Influenza Viruses Mice were divided into 5 groups, and the non-vaccinated or vaccinated groups were challenged with each of four heterologous influenza viruses. Then, protection efficacy of the vaccines was evaluated through changes in weight and survival rate of the mice.

As a result, after infection with the four viruses, the non-vaccinated mice exhibited 100% mortality in 8 days while showing rapid weight loss (FIG. 5A). On the other hand, all mice vaccinated with a live vaccine survived (FIGS. 5B to 5E).

Figure 5:
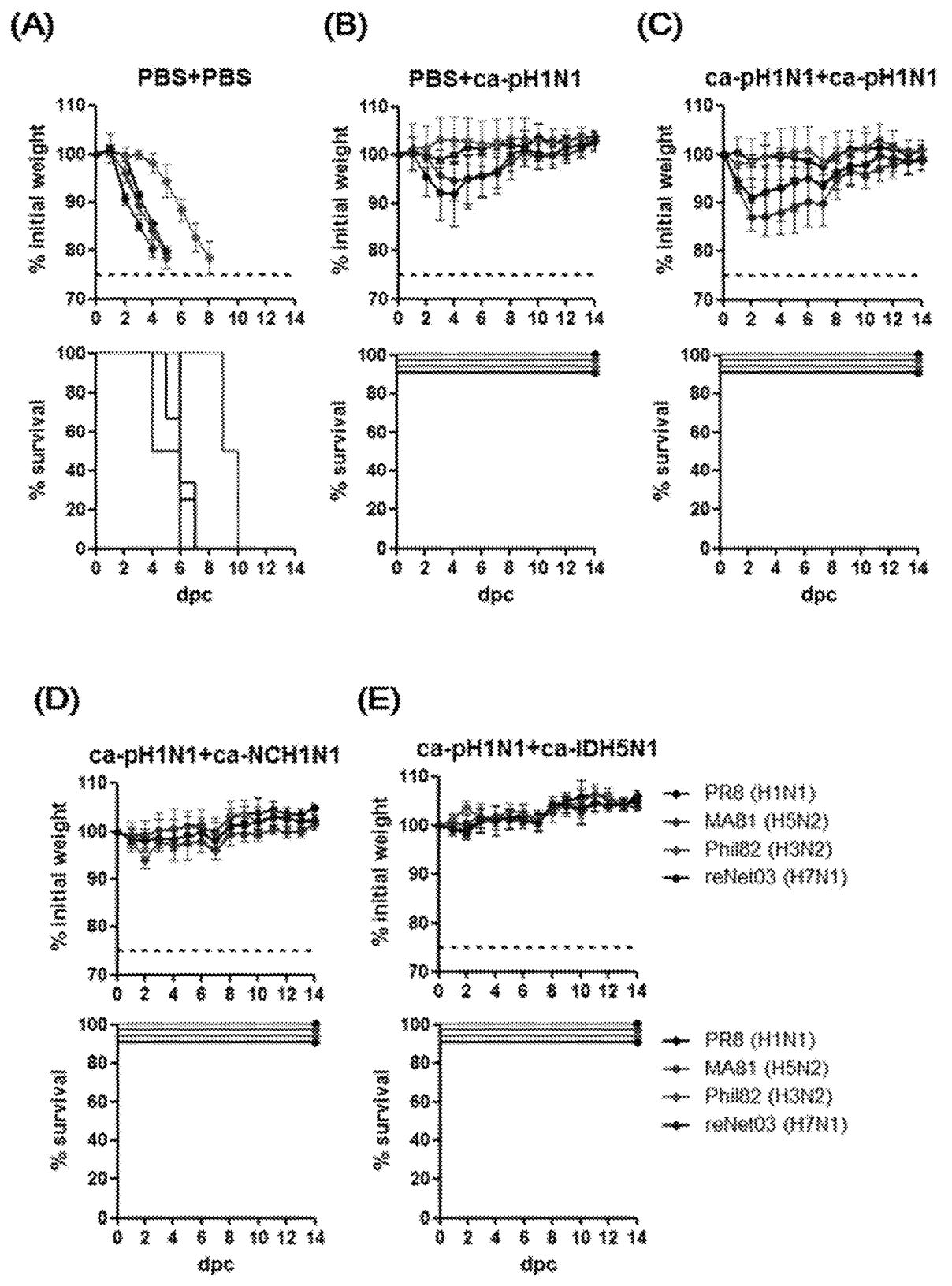

Specifically, at the time of single vaccination with a live vaccine, a weight loss within 1% was exhibited against infection with PR8 (H1N1) or Phil82 (H3N2), and a weight loss of 5% to 8% was exhibited against infection with MA81 (H5N2) or reNet03 (H7N1) (FIG. 5B). At the time of additional vaccination with a homologous live vaccine, a similar level of weight loss to the single vaccination was exhibited against infection with PR8 (H1N1), Phil82 (H3N2), or reNet03 (H7N1); on the other hand, a weight loss of 12.9% was exhibited against infection with MA81 (H5N2) virus, which rather represents about 2-fold loss in weight as compared with the single vaccination with live vaccine (FIG. 5C). However, boost vaccination using a heterologous live vaccine resulted in a perfect protection without any loss in weight. In a case of being additionally vaccinated with ca-NCH1N1, a weight loss of 5% was exhibited against infection with MA81 (H5N2) virus, which represents a similar weight loss to that exhibited at the time of the single vaccination, but a faster recovery rate was exhibited (FIG. 5D). In a case of being additionally vaccinated with ca-IDH5N1, a perfect protection ability without any loss in weight was exhibited against infection with four heterologous influenza viruses, and thus the best cross-protective ability was exhibited (FIG. 5E).

From this, it was found that 1) even single vaccination with a live vaccine can provide protection against all viruses of HA groups 1 and 2, and, however, 2) double vaccination with heterologous live vaccines can remarkably improve efficacy and range of cross-protection against heterologous influenza viruses as compared with the single vaccination.

For example, in a case where reNet03 (H7N1) virus is used for challenge, a weight loss of 8% was exhibited at the time of single vaccination with a live vaccine, whereas increased protection efficacies were exhibited, with a weight loss of 2% at the time of additional vaccination with ca-NCH1N1 and a weight loss of 1% at the time of additional vaccination with ca-IDH5N1, respectively. In a case where values of weight loss are considered as protection efficacy, the values can be quantified as protection efficacy-increasing effects of 400% and 800%, respectively. On the other hand, in a case of MA81 (H5N2) virus, a weight loss of 5% was observed at the time of single vaccination with a live vaccine, but no weight loss (0%) was exhibited at the time of additional vaccination with heterologous ca-IDH5N1, which can be regarded as a remarkable increase in protection efficacy of equal to or greater than 500%.

Figure 6:
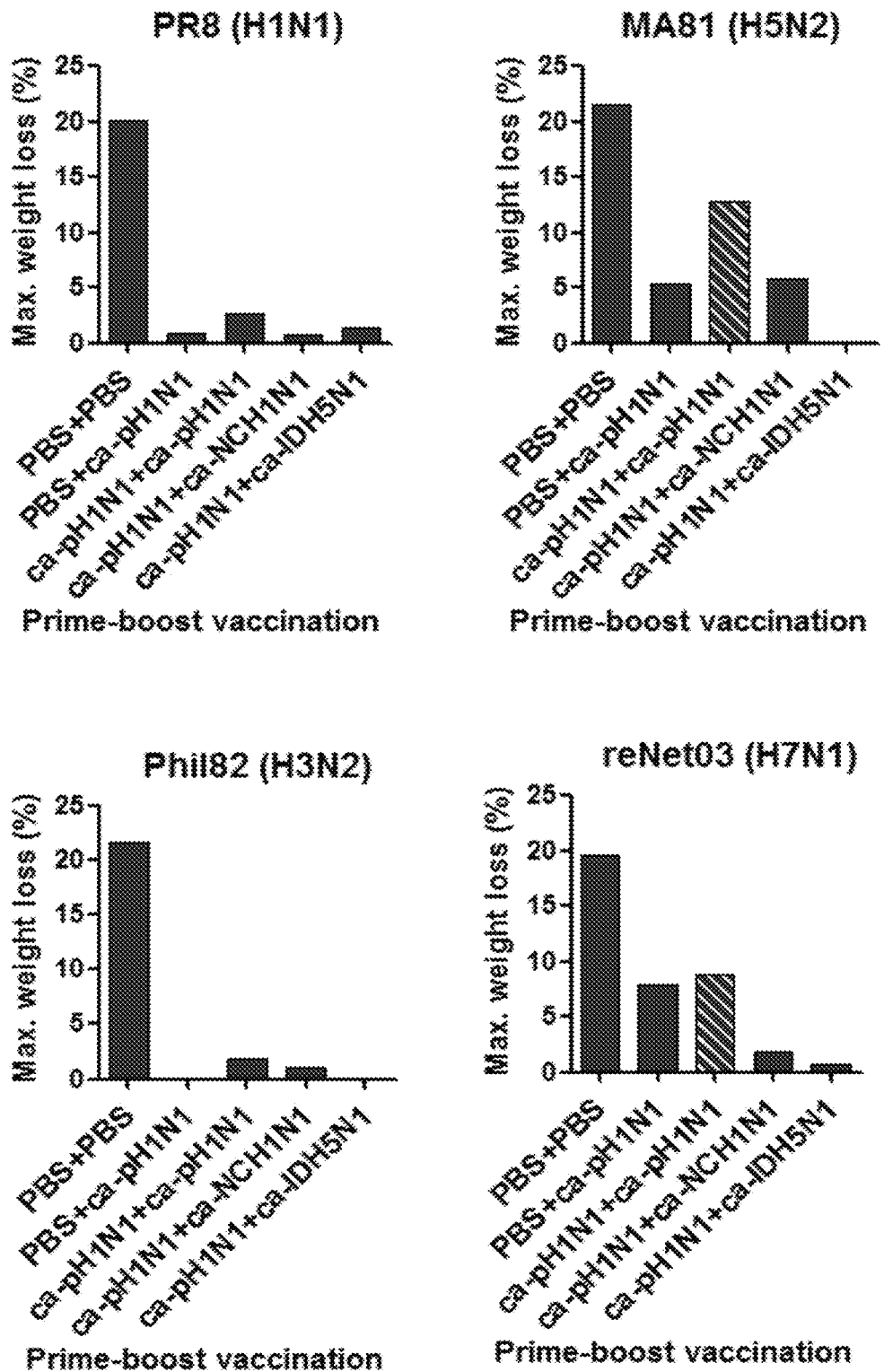

The maximum weight loss in mice after the challenges is summarized in FIG. 6. For challenges with H5N2 and H7N1 viruses, it was found that there is a pathological phenomenon of increased weight loss at the time of double vaccination with homologous live vaccines as compared with single vaccination. However, this phenomenon was greatly improved through a method of performing additional vaccination with a heterologous vaccine, and this improvement was demonstrated in all four different challenges (PR8 (H1N1), MA81 (H5N2), Phil82 (H3N2), and reNet03 (H7N1)). Specifically, in a case where a relative comparison was made for weight loss (%), it was found that protection efficacy increases by 200% to 400% for PR8 (H1N1); 250% or more for MA81 (H5N2); 200% or more for Phil82 (H3N2); and 400% to 800% or more for reNet03 (H7N1).

Figure 7:
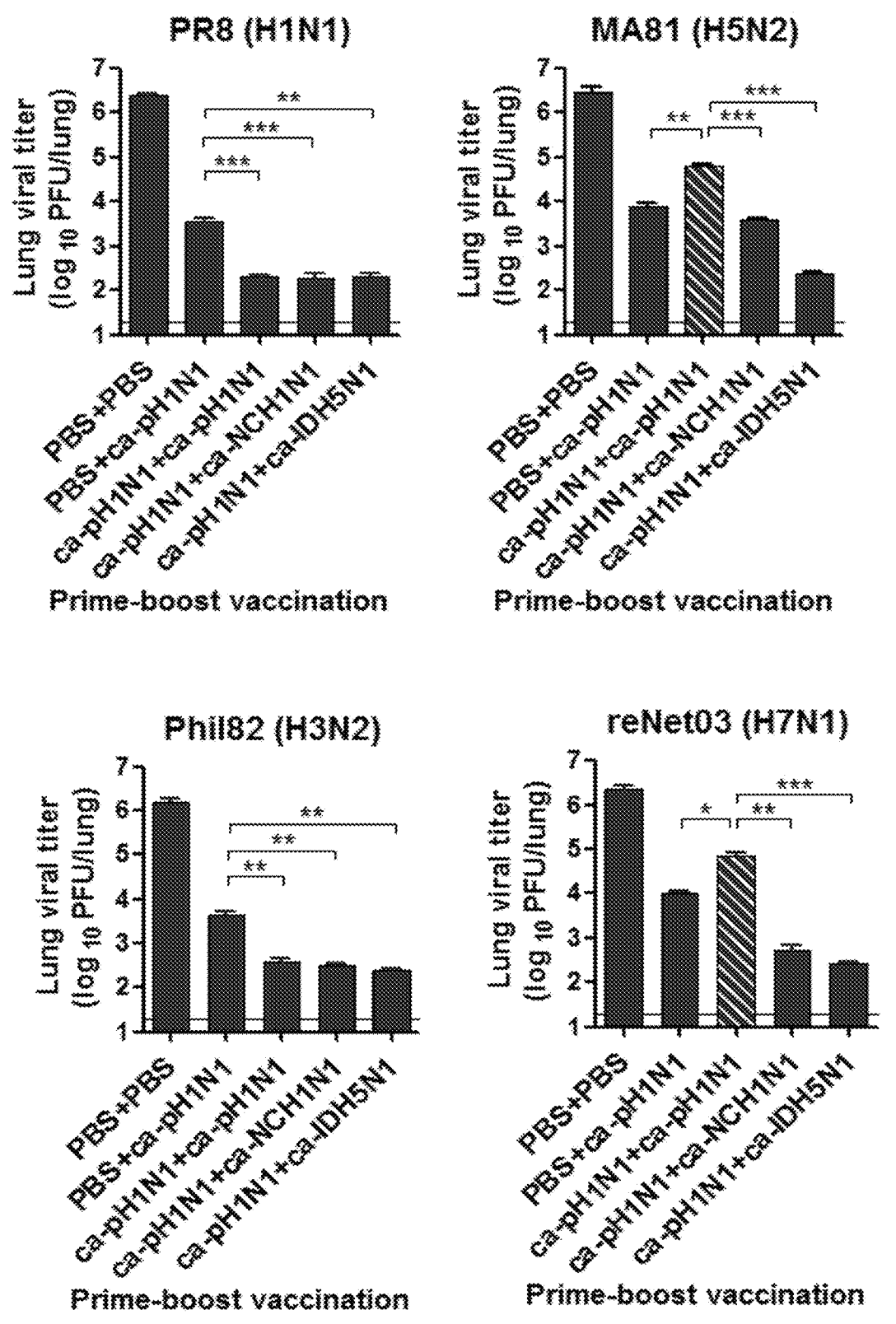

In addition, non-vaccinated and vaccinated mice (n=5) were challenged with four heterologous influenza viruses. After 6 days, the lungs of mice were collected to measure viral titers in lung tissues. As a result, as shown in FIG. 7, viral titers were decreased by 100 times or more in all vaccinated groups as compared with the non-vaccinated groups. In contrast with one single vaccination, in a case of being additionally vaccinated with heterologous vaccine, an effect of decreasing viral titers by about 10 to 50 times was exhibited against all four different viruses. In addition, a phenomenon where viral titers against H7N1 and H5N2 viruses are increased at the time of double vaccination with homologous live vaccines as compared with single vaccination shows the results which are consistent with the results of changes in weight of mice (FIG. 6). Therefore, from this, it was found that double vaccination with heterologous live vaccines is most effective for cross-protection against various influenza viruses.

Example 5. Assay for Memory CTL Activity after Infection with Viruses

An assay for memory cytotoxic T-lymphocyte (CTL) activity, which recognizes the $NP_{147-155}$ (TYQRTRALV) epitope that is conserved among influenza A viruses, was performed. Specifically, one month after double vaccination with live vaccines, challenge with PR8 (H1N1) or Phil82 (H3N2) was performed. Mouse blood was collected on days 0 (before challenge), 2, 4, and 6 from the day of challenge, and lung tissue was collected on day 6. Then, flow cytometric analysis was performed to measure CD8+ CTL frequency (FIG. 8A).

Figure 8:
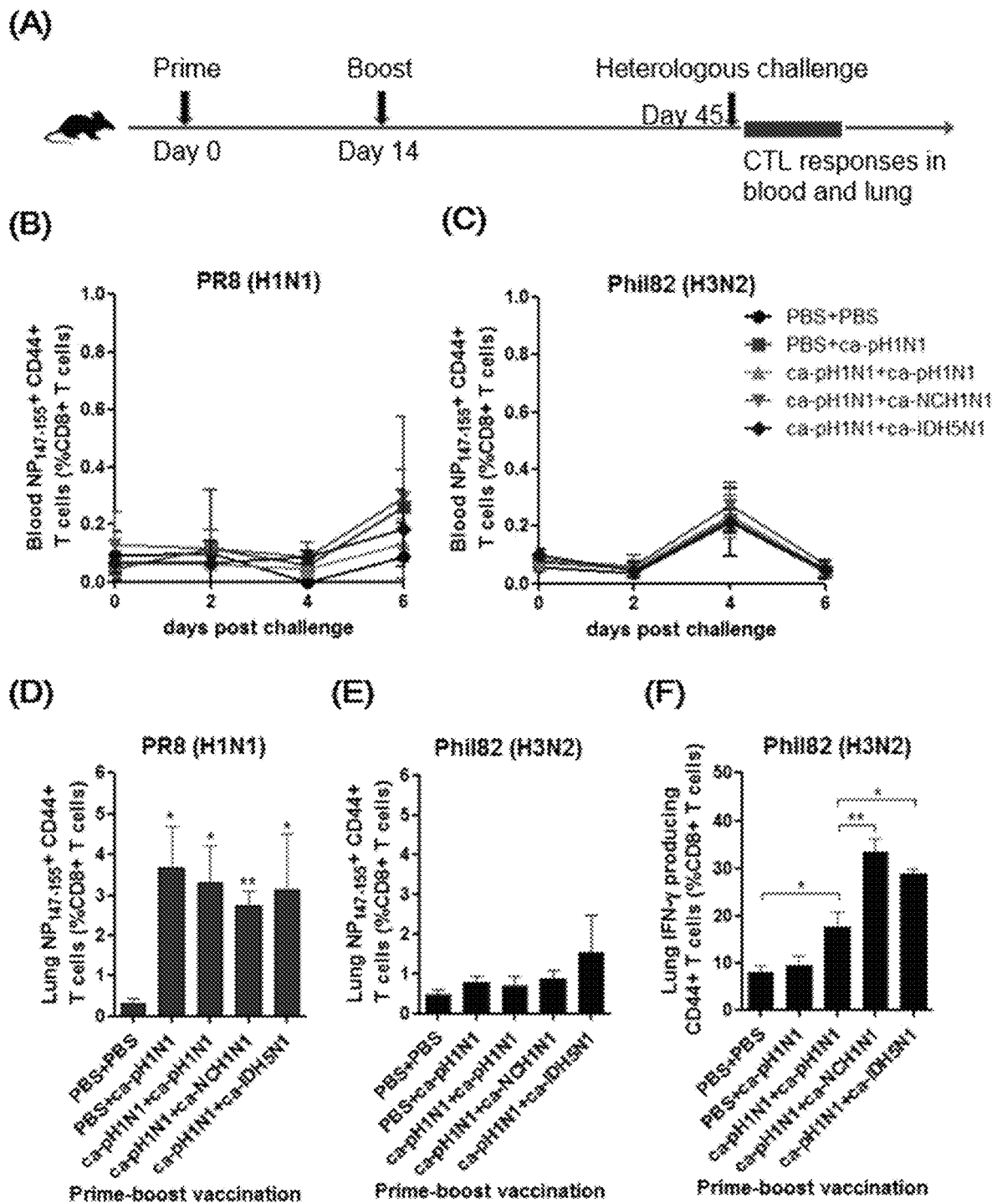

As a result, no significant CTL increase in the blood after virus infection with viruses was exhibited in the vaccinated groups as compared with the non-vaccinated groups (FIGS. 8B and 8C). However, in the lungs, 7- to 10-fold increased CTL was exhibited in the vaccinated groups as compared with the non-vaccinated control group after infection with H1N1 virus (FIG. 8D). CTL frequency increased even after infection with H3N2 virus. However, there was no statistical significance (FIG. 8E). On the other hand, after infection with H3N2 virus, 2- to 4-fold increased IFN-γ-secreting CTL was exhibited in the vaccinated group as compared with the control group. From this, it was found that CTLs which recognize other epitopes in addition to the $NP_{147-155}$ epitope are increased (FIG. 8F). IFN-γ-secreting CTL is increased in the order of single vaccination with a live vaccine (9.4%)<double vaccination with homologous live vaccines (18%)<double vaccination with heterologous live vaccines (29% to 33%). From this, it was found that the double vaccination with heterologous live vaccines is also very effective for eliciting T cell-mediated immune response against heterologous influenza viruses.

Example 6. Assay for Cross-Protective Contribution of T Cells and NK Cells

Figure 9A:
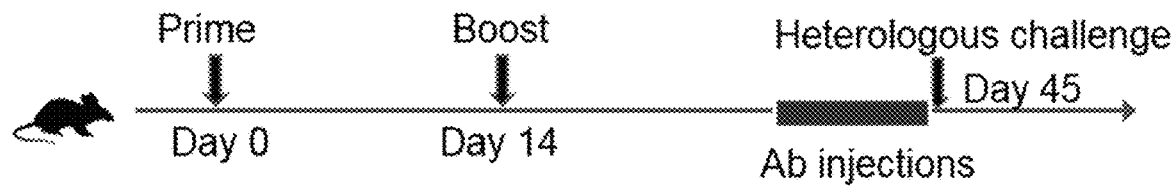
Figure 9B:
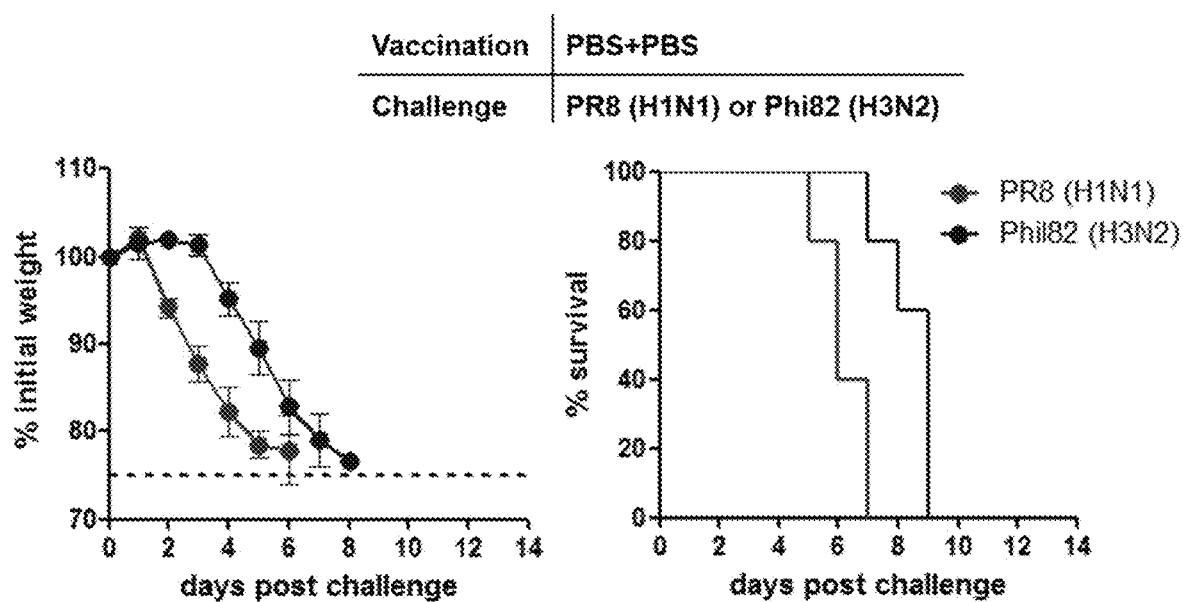

The vaccinated mice were administered a depleting antibody to deplete CD4+ T cells, CD8+ T cells, and NK cells, and then infected with PR8 (H1N1) or Phil82 (H3N2) virus (FIG. 9A). Specifically, in order to deplete CD4+ T cells and CD8+ T cells, mice were intraperitoneally administered 4 times (1, 3, 5, and 7 days before challenge) 200 µg of anti-CD8 mAb (clone 2.43; BioXcell) and anti-CD4 mAb (clone GK1.5; BioXcell). Control mice were administered isotype control IgG2b antibodies (clone LTF-2, BioXcell). Twenty-four hours after the last antibody injection, the blood and lungs of the mice were collected, and flow cytometric analysis was performed to identify T cell depletion. For the flow cytometric analysis, anti-CD8 mAb (clone 53-6.7; BioLegend) and anti-CD4 mAb (clone RM4-5; BioLegend) were used. For NK cell depletion, 20 µl of anti-asialo GM1 antiserum (Wako Pure Chemical Industries, Ltd.) was injected into the mice in the same manner. Control mice were administered normal rabbit serum (Wako Pure Chemical Industries, Ltd.). Twenty-four hours after the last antibody injection, the spleens were collected, and flow cytometric analysis was performed using anti-CD3 mAb (clone 17A2; Biolegend) and anti-CD49b mAb (clone DX5; Biolegend), to identify NK cell depletion.

Figure 9C:
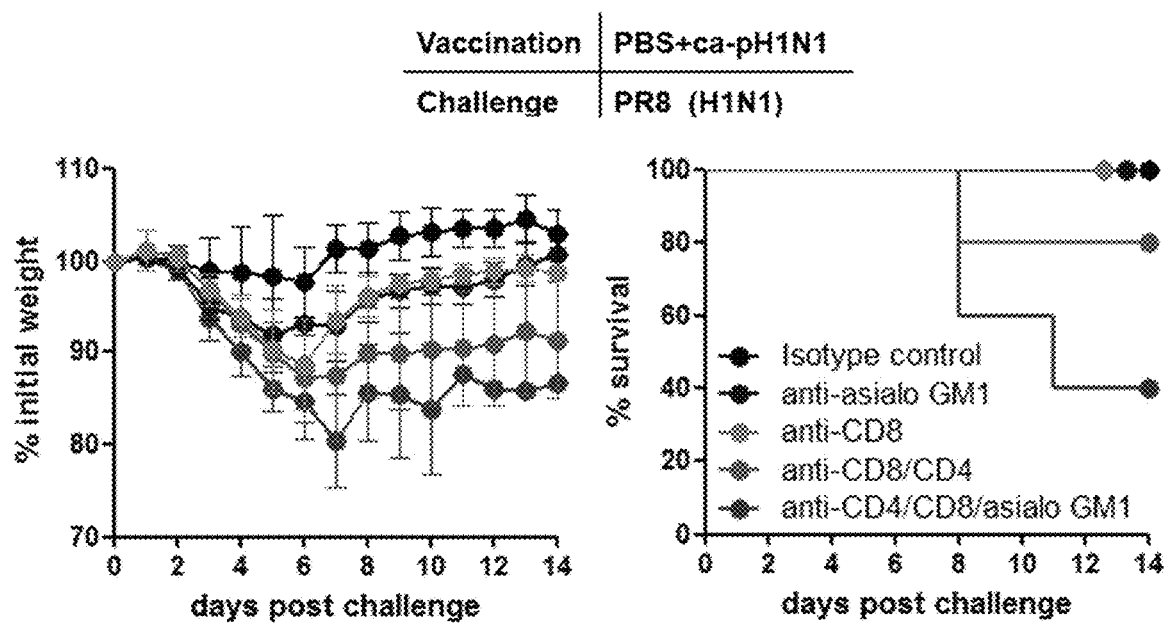
Figure 9D:
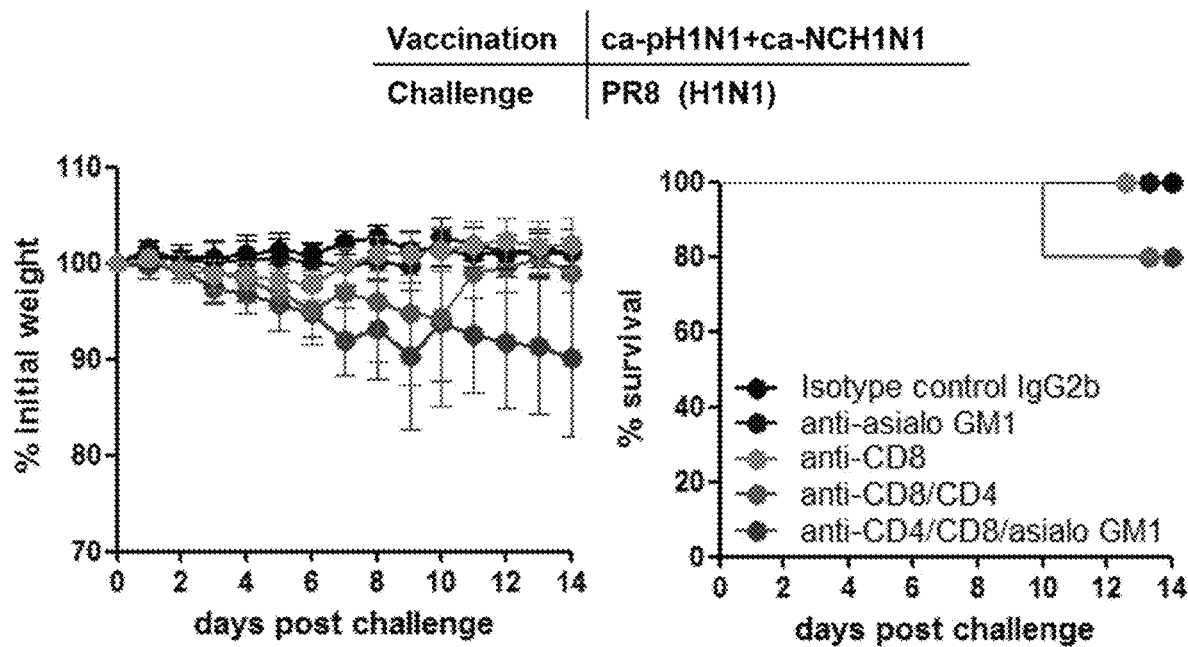
Figure 9E:
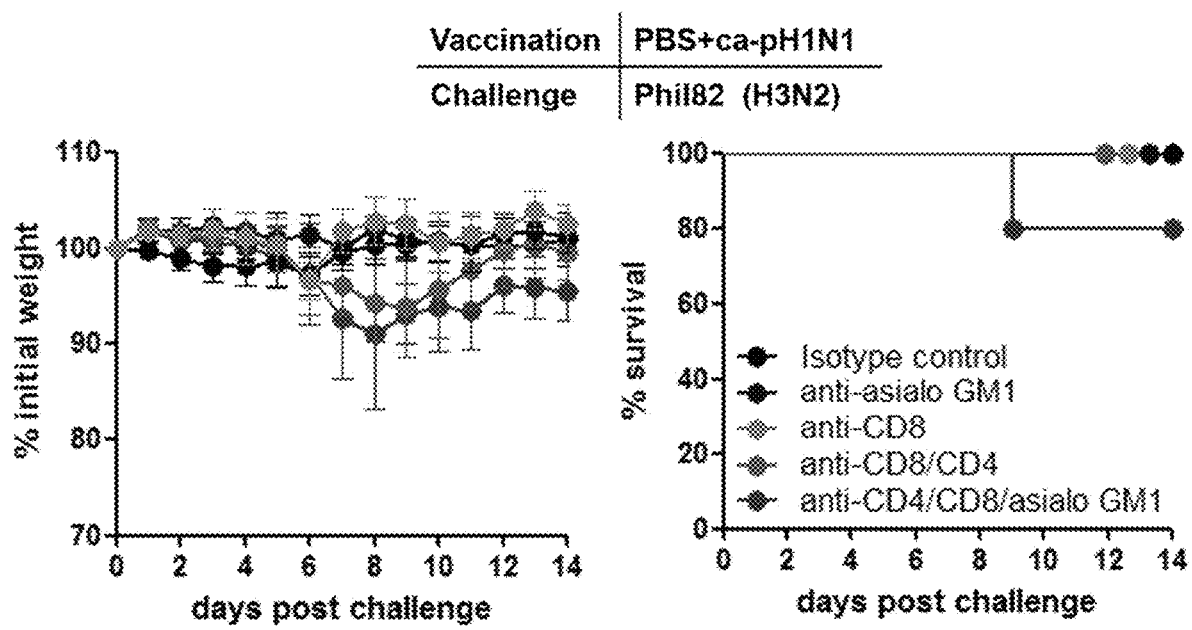
Figure 9F:
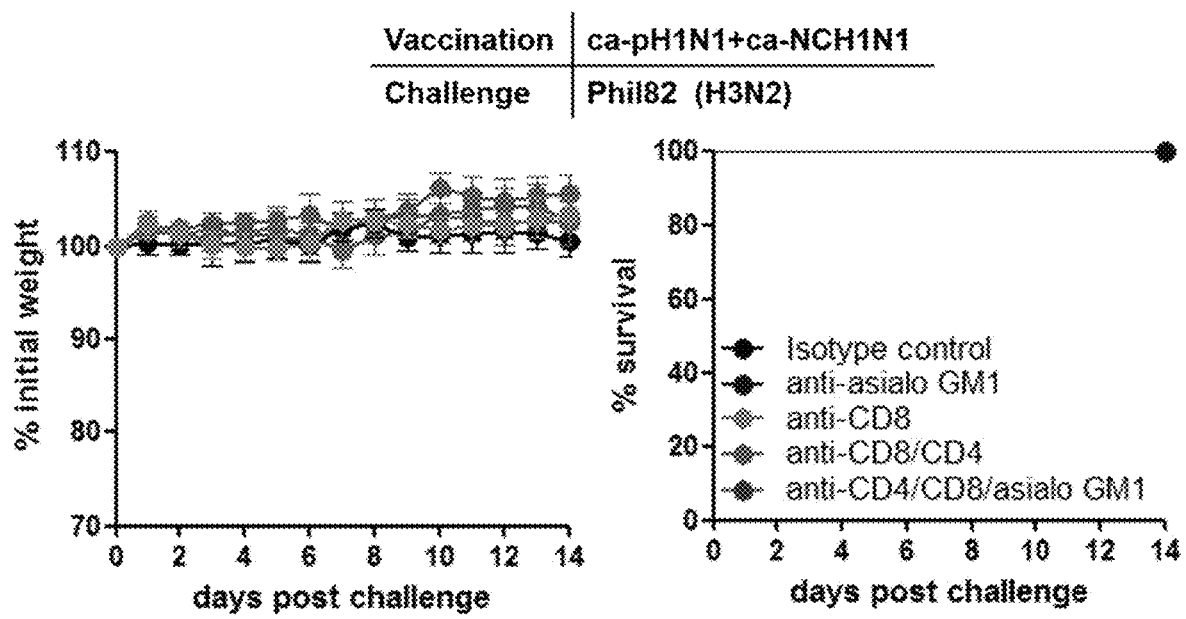

First, after the infection with H1N1 virus in the groups receiving single vaccination with a live vaccine, almost no weight loss was exhibited in the control (non-depleted) mice, but a weight loss of about 11% was exhibited in the absence of CD8+ T cells. In the absence of both CD8+ T cells and CD4+ T cells, a weight loss of about 13% and 20% mortality were exhibited and a slow weight recovery was exhibited in survived mice. From this, it was found that both CD8+ T cells and CD4+ T cells contribute to cross-protection. In the absence of NK cells, a similar weight loss to that in the absence of CD8+ T cells was exhibited. In the absence of all T cells and NK cells, a weight loss of 20% body and 60% mortality were exhibited. From this, it was found that NK cells also contribute to cross-protection (FIG. 9C). In the groups receiving double vaccination with heterologous live vaccines, in the absence of all T cells and NK cells, a weight loss of 10% and 20% mortality were exhibited after infection with H1N1 virus (FIG. 9D). In the groups receiving single vaccination with a live vaccine, in the absence of all T cells and NK cells, a weight loss of 10% and 20% mortality were exhibited after infection with H3N2 virus (FIG. 9E). At the time of double vaccination with heterologous live vaccines, despite the absence of all T cells and NK cells, no weight loss was exhibited after infection with H3N2 virus (FIG. 9F).

From these results, it was found that T cells and NK cells respectively contribute to cross-protection, and that other mechanism in addition to this contribute to cross-protection. From the results that even in the absence of NK cells and T cells, as compared with the single vaccination with a live vaccine, protection efficacy was further increased in the double vaccination, it was found that there is a separate cross-protective mechanism mediated by vaccination-induced antibodies.

Example 7. Verification of Vaccine Safety

In order to investigate whether non-neutralizing antibodies cause a phenomenon of increased infectivity of heterologous influenza viruses, MDCK and RAW264.7 cells were infected with a mixed solution of serum and virus, and then a degree of infection with virus was measured by NP-based ELISA.

Figure 10A:
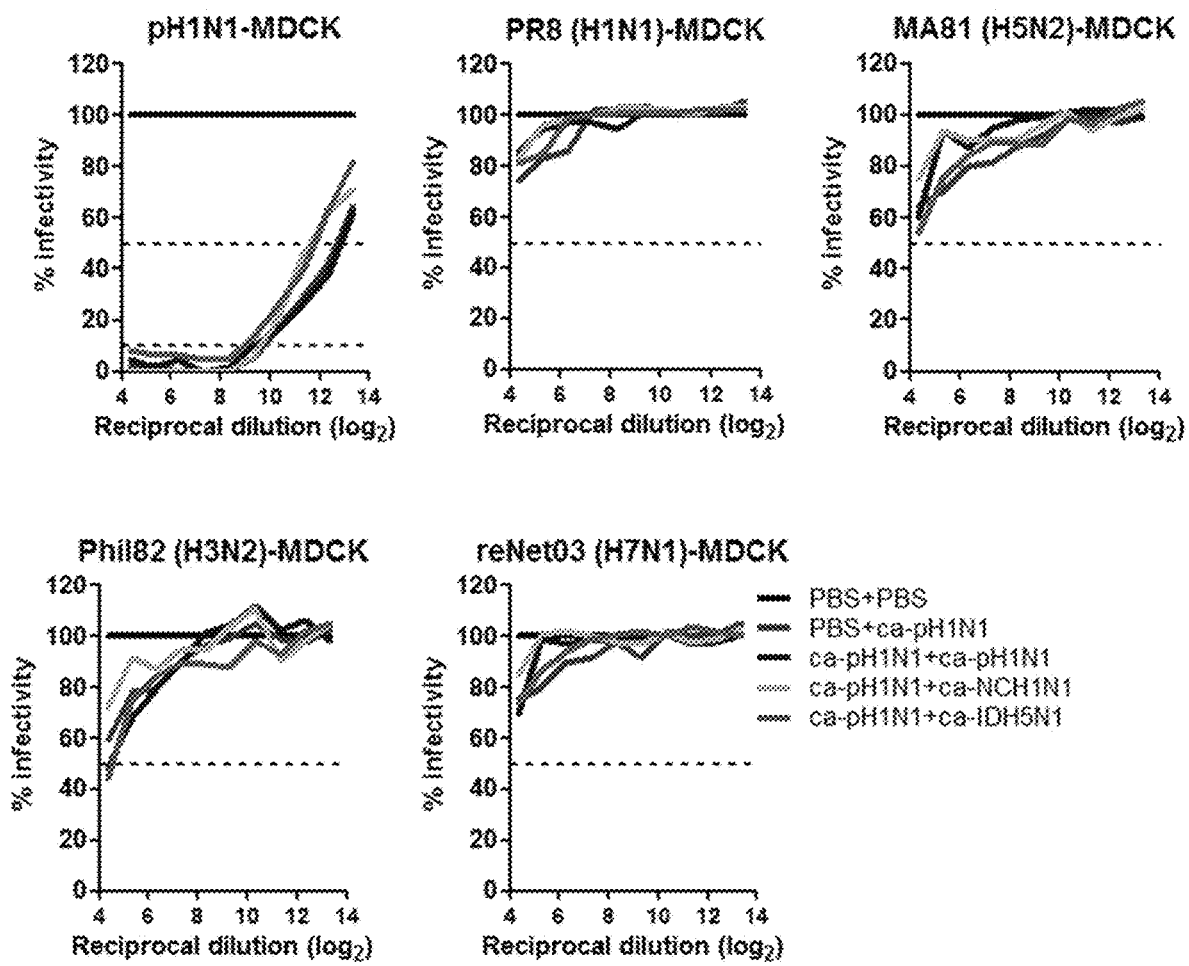
Figure 10B:
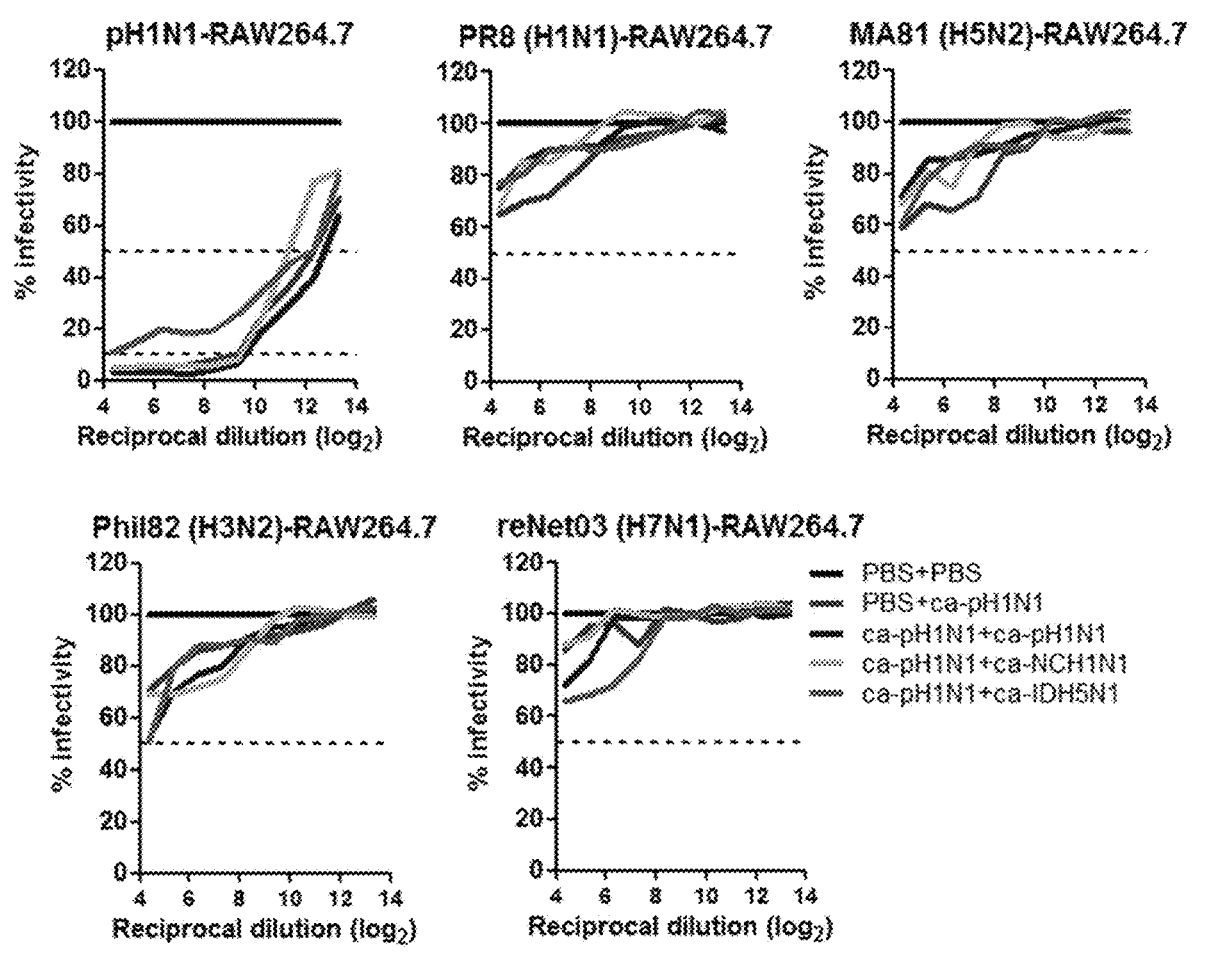

As a result, in both cell lines, the vaccine-induced antibodies effectively suppressed replication of pH1N1 virus which is a virus homologous to the vaccine strain, and also suppressed proliferation of four heterologous influenza viruses by 50% to 85%. However, such vaccine-induced antibodies did not increase infectivity of these viruses as compared with the non-vaccine-induced antibodies. These results indicate that a phenomenon of increased infectivity occurring in the conventional HA stalk-based vaccines does not occur in the vaccines of the present invention (FIGS. 10A and 10B).

In addition, in order to check whether an immune interference effect between heterologous live vaccines causes a phenomenon of inhibited antibody response, the live vaccine used as the secondary vaccine strain was vaccinated once and then the neutralizing antibody titer thereof was compared with the neutralizing antibody titer obtained after double vaccination with live vaccines.

Figure 10C:
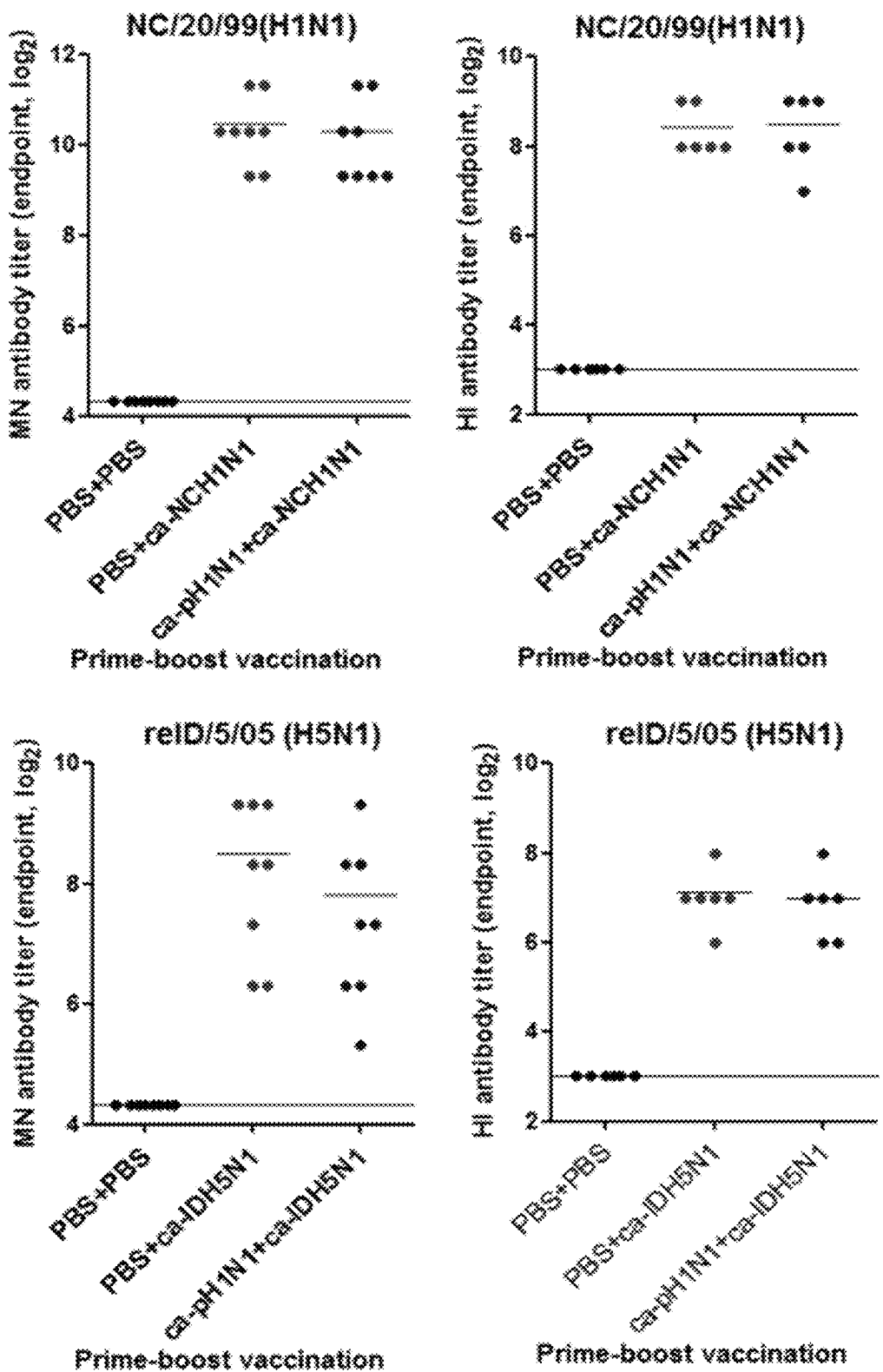

As a result, MN and HI antibody titers were similar to each other between the two experimental conditions. From this, it was found that inhibited antibody response is not caused by an immune interference at the time of double vaccination with heterologous live vaccines (FIG. 10C). This means that the vaccines used in the present study and the additional vaccination methods with heterologous vaccines based on such vaccines are very safe.

What is claimed is:

1. A prime-boost vaccination method for influenza viruses by producing a cross-immune response against at least one HA protein (HA group 1) selected from the group consisting of H1, H2, H5, H6, H8, H9, H11, H12, H13, and H16; and at least one HA protein (HA group 2) selected from the group consisting of H3, H4, H7, H10, H14, and H15, the method comprising:

(a) administering a first influenza live vaccine that carries six internal genes represented by SEQ ID NOS: 1 to 6; A/Korea/1/09 (H1N1) influenza virus-derived surface hemagglutinin (HA) gene represented by SEQ ID NO: 7; and A/Korea/1/09 (H1N1) influenza virus-derived surface neuraminidase (NA) gene represented by SEQ ID NO: 8; and (b) administering a second influenza live vaccine that carries six internal genes represented by SEQ ID NOS: 1 to 6; A/New Caledonia/20/99 (H1N1) influenza virus-derived surface hemagglutinin (HA) gene represented by SEQ ID NO: 9; and A/New Caledonia/20/99 (H1N1) influenza virus-derived surface neuraminidase (NA) gene represented by SEQ ID NOS: 10, wherein the first influenza live vaccine and the second influenza live vaccine contain viruses that carry HA and NA genes which are heterologous and homosubtypic to each other.

* * * * *

SEQUENCE LISTING

<160> NUMBER OF SEQ ID NOS: 12

<210> SEQ ID NO 1
<211> LENGTH: 2295
<212> TYPE: DNA
<213> ORGANISM: Artificial Sequence
<220> FEATURE:
<223> OTHER INFORMATION: DQ874873 (X-31 ca PB2)

<400> SEQUENCE: 1

```
ttcaatatgg aaagaataaa agaactacga aatctaatgt cgcagtctcg cacccgcgag      60
atactcacaa aaaccaccgt ggaccatatg gccataatca agaagtacac atcaggaaga     120
caggagaaga acccagcact taggatgaaa tggatgatgg caatgaaata tccaattaca     180
gcagacaaga ggataacgga aatgattcct gagagaaatg agcaaggaca aactttatgg     240
agtaaaatga atgatgccgg atcagaccga gtgatggtat cacctctggc tgtgacatgg     300
tggaatagga atgaccaat aacaaataca gttcagtatc caaaaatcta caaaacttat     360
tttgaaagag tcgaaaggct aaagcatgga acctttggcc ctgtccattt tagaaaccaa     420
gtcaaaatac gtcggagagt tgacataaat cctggtcatg cagatctcag tgccaaggag     480
gcacaggatg taatcatgga agttgttttc cctaacgaag tgggagccag gatactaaca     540
tcggaatcgc aactaacgat aaccaaagag aagaaagaag aactccagga ttgcaaaatt     600
tctcctttga tggttgcata catgttggag agagaactgg tccgcaaaac gagattcctc     660
ccagtggctg gtgaacaag cagtgtgtac attgaagtgt tgcatttgac tcaaggaaca     720
tgctgggaac agatgtatac tccaggaggg gaagtgagga atgatgatgt tgatcaaagc     780
```

```
ttgattattg ctgctaggaa catagtgaga agagctgcag tatcagcaga tccactagca    840
tctttattgg agatgtgcca cagcacacag attggtggaa ttaggatggt agacatcctt    900
aggcagaacc caacagaaga gcaagccgtg gatatatgca aggctgcaat gggactgaga    960
attagctcat ccttcagttt tggtggattc acatttaaga gaacaagcgg atcatcagtc   1020
aagagagagg aagaggtgct tacgggaaat cttcaaacat tgaagataag agtgcatgag   1080
ggatatgaag agttcacaat ggttgggaga agagcaacag ccatactcag aaaagcaacc   1140
aggagattga ttcagctgat agtgagtggg agagacgaac agtcgattgc cgaagcaata   1200
attgtggcca tggtattttc acaagaggat tgtatgataa agcagtcag aggtgatctg    1260
aatttcgtca atagggcgaa tcagcgattg aatcctatgc atcaacttt aagacatttt    1320
cagaaggatg cgaaagtgct ttttcaaaat tggggagttg aacctatcga caatgtgatg   1380
ggaatgattg ggatattgcc cgacatgact ccaagcatcg agatgtcaat gagaggagtg   1440
agaatcagca aaatgggtgt agatgagtac tccagcacgg agagggtagt ggtgagcatt   1500
gaccgttttt tgagaatccg ggaccaacga ggaaatgtac tactgtctcc cgaggaggtc   1560
agtgaaacac agggaacaga gaaactgaca ataacttact catcgtcaat gatgtgggag   1620
attaatggtc ctgaatcagt gttggtcaat acctatcaat ggatcatcag aaactgggaa   1680
actgttaaaa ttcagtggtc ccagaacccc acaatgctat acaataaaat ggaatttgaa   1740
ccatttcagt ctttagtacc taaggccagt agaggccaat acagtgggtt tgtaagaact   1800
ctgttccaac aaatgagga tgtgcttggg acatttgata ccgcacagat aataaaactt   1860
cttcccttcg cagccgctcc accaaagcaa agtagaatgc agttctcctc atttactgtg   1920
aatgtgaggg atcaggaat gagaatactt gtaaggggca attctcctgt attcaactat   1980
aacaaggcca cgaagagact cacagttctc ggaaaggatg ctggcacttt aactgaagac   2040
ccagatgaag gcacagctgg agtggagtcc gctgttctga ggggattcct cattctgggc   2100
aaagaagaca agagatatgg gccagcacta agcatcaatg aactgagcaa ccttgcgaaa   2160
ggagagaagg ctaatgtgct aattgggcaa ggagacgtgg tgttggtaat gaaacggaaa   2220
cgggactcta gcatacttac tgacagccag acagcgacca aagaattcg gatggccatc   2280
aattagtgtt gaata                                                   2295
```

<210> SEQ ID NO 2
<211> LENGTH: 2303
<212> TYPE: DNA
<213> ORGANISM: Artificial Sequence
<220> FEATURE:
<223> OTHER INFORMATION: DQ874874 (X-31 ca PB1)

<400> SEQUENCE: 2

```
ttgaatggat gtcaatccga ccttactttt cttaaaagtg ccagcacaaa atgctataag    60
cacaactttc ccttatactg gagaccctcc ttacagccat gggacaggaa caggatacac   120
catggatact gtcaacagga cacatcagta ctcagaaaag ggaagatgga caacaaacac   180
cgaaactgga gcaccgcaac tcaacccgat tgatgggcca ctgccagaag acaatgaacc   240
aagtggttat gcccaaacag attgtgtatt ggaggcgatg gctttccttg aggaatccca   300
tcctggtatt tttgaaaact cgtgtattga acgatggag gttgttcagc aaacacgagt   360
agacaagctg acacaaggcc gacagaccta tgactggact ctaaatagaa accaacctgc   420
tgcaacagca ttggccaaca caataagagt gttcagatca aatggcctca ggccaatga    480
gtctggaagg ctcatagact tccttaagga tgtaatggag tcaatgaaca aagaagaaat   540
```

-continued

```
ggggatcaca actcatttc agagaaagag acgggtgaga cacaatatga ctaagaaaat      600
gataacacag agaacaatgg gtaaaagaa gcagagattg aacaaaagga gttatctaat      660
tagagcattg accctgaaca caatgaccaa agatgctgag agagggaagc taaaacggag    720
aacaattgca accccaggga tgcaaataag ggggtttgta tactttgttg agacactggc    780
aaggagtata tgtgagaaac ttgaacaatc agggttgcca gttggaggca atgagaagaa    840
agcaaagttg gcaaatgttg taaggaagat gatgaccaat tctcaggaca ccgaactttc    900
tttcaccatc actggagata caccaaatg gaacgaaaat cagaatcctc ggatgttttt     960
ggccatgatc acatatatga ccagaaatca gcccgaatgg ttcagaaatg ttctaagtat  1020
tgctccaata atgttctcaa acaaaatggc gagactggga aagggtata tgtttgagag   1080
caagagtatg aaacttagaa ctcaaatacc tgcagaaatg ctagcaagca tcgatttgaa  1140
atatttcaat gattcaacaa gaagaagat tgaaaaaatc cgaccgctct aatagaggg    1200
gactgcatca ttgagccctg aatgatgat gggcatgttc aatatgttga gcactgtatt   1260
aggcgtctcc atcctgaacc ttggacaaaa gagatacacc aagactactt actggtggga  1320
tggtcttcaa tcctctgacg attttgctct gattgtgaat gcacccaatc atgaagggat  1380
tcaagccgga gtcgacaggt tttatcgaac ctgtaagcta cttggaatca atatgagcaa  1440
gaaaaagtct tacataaaca gaacaggtac atttgaattc acaagttttt tctatcgtta  1500
tgggtttgtt gccaatttca gcatggagct tcccagtttt ggggtgtctg ggatcaacga  1560
gtcagcggac atgagtattg gagttactgt catcaaaaac aatatgataa acaatgatct  1620
tggtccagca acagctcaaa tggcccttca gttgttcatc aaagattaca ggtacacgta  1680
ccgatgccat agaggtgaca cacaaataca aacccgaaga tcatttgaaa taagaaaact  1740
gtgggagcaa acccgttcca aagctggact gctggtctcc gacggaggcc caaatttata  1800
caacattaga aatctccaca ttcctgaagt ctgcctaaaa tgggaattga tggatgagga  1860
ttaccagggg cgtttatgca acccactgaa ccccattgtc agccataaag aaattgaatc  1920
aatgaacaat gcagtgatga tgccagcaca tggtccagcc aaaaacatgg agtatgatgc  1980
tgttgcaaca acacactcct ggatccccaa aagaaatcga tccatcttga atacaagtca  2040
aagaggagta cttgaggatg aacaaatgta ccaaggtgc tgcaatttat ttgaaaaatt  2100
cttccccagc agttcataca gaagaccagt cgggatatcc agtatggtgg aggctatggt  2160
ttctagagcc cgaattgatg cacggattga tttcgaatct ggaaggataa agaaagaaga  2220
gttcactgag atcatgaaga tctgttccac cattgaagag ctcagacggc aaaaatagtg  2280
aatttagctt gtccttcatg aaa                                          2303
```

<210> SEQ ID NO 3
<211> LENGTH: 2196
<212> TYPE: DNA
<213> ORGANISM: Artificial Sequence
<220> FEATURE:
<223> OTHER INFORMATION: DQ874875 (X-31 ca PA)

<400> SEQUENCE: 3

```
ccaaaatgga agattttgtg cgacaatgct tcaatccgat gattgtcgag cttgcggaaa      60
aaacaatgaa agagtatggg gaggacctga aaatcgaaac aaacaaattt gcagcaatat    120
gcactcactt ggaagtatgc ttcatgtatt cagattttca cttcatcaat gagcaaggcg    180
agtcaataat cgtagaactt ggtgatccaa atgcactttt gaagcacaga tttgaaataa    240
tcgagggaag agatcgcaca atggcctgga cagtagtaaa cagtatttgc aacactacag    300
```

```
gggctgagaa accaaagttt ctaccagatt tgtatgatta caaggagaat agattcatcg      360
aaattggagt aacaaggaga gaagttcaca tatactatct ggaaaaggcc aataaaatta      420
aatctgagaa acacacatc cacattttct cgttcactgg ggaagaaatg ccacaaagg       480 cagactacac tctcgatgaa gaaagcaggg ctaggatcaa aaccagacta ttcaccataa      540
gacaagaaat ggccagcaga ggcctctggg attccttcg tcagtccgag agaggagaag      600
agacaattga gaaaggtttt gaatcacag gaacaatgcg caagcttgcc gaccaaagtc      660
tcccgccgaa cttctccagc cttgaaaatt ttagagccta tgtggatgga ttcgaaccga      720
acggctacat tgagggcaag ctgtctcaaa tgtccaaaga agtaaatgct agaattgaac      780
cttttttgaa aacaacacca cgaccactta gacttccgaa tgggcctccc tgttctcagc      840
ggtccaaatt cctgctgatg gatgccttaa aattaagcat tgaggaccca agtcatgaag      900
gagagggaat accgctatat gatgcaatca aatgcatgag aacattcttt ggatggaagg      960
aacccaatgt tgttaaacca cacgaaaagg gaataaatcc aaattatctt ctgtcatgga     1020
agcaagtact ggcagaactg caggacattg agaatgagga gaaaattcca aagactaaaa     1080
atatgaagaa aacaagtcag ctaaagtggg cacttggtga gaacatggca ccagaaaagg     1140
tagactttga cgactgtaaa gatgtaggtg atttgaagca atatgatagt gatgaaccag     1200
aattgaggtc acttgcaagt tggattcaga atgagtttaa caaggcatgc gaactgacag     1260
attcaagctg gatagagctc gatgagattg agaagatgt ggctccaatt gaacacattg     1320
caagcatgag aaggaattat ttcacatcag aggtgtctca ctgcagagcc acagaataca     1380
taatgaaggg agtgtacatc aatactgcct tgcttaatgc atcttgtgca gcaatggatg     1440
atttccaatt aattccaatg ataagcaagt gtagaactaa ggagggaagg cgaaagacca     1500
acttgtatgg tttcatcata aaaggaagat cccacttaag gaatgacacc gacgtggtaa     1560
actttgtgag catggagttt tctctcactg acccaagact tgaaccacat aaatgggaga     1620
agtactgtgt tcttgagata ggagatatgc ttataagaag tgccataggc caggtttcaa     1680
ggcccatgtt cttgtatgtg agaacaaatg gaacctcaaa aattaaaatg aaatggggaa     1740
tggagatgag gcgttgcctc ctccagtcac ttcaacaaat tgagagtatg attgaagctg     1800
agtcctctgt caaagagaaa gacatgacca aagagttctt tgagaacaaa tcagaaacat     1860
ggcccattgg agagtccccc aaaggagtgg aggaaagttc cattgggaag gtctgcagga     1920
ctttattagc aaagtcggta ttcaacagct tgtatgcatc tccacaacta gaaggatttt     1980
cagctgaatc aagaaaactg ctcttgtcg ttcaggctct tagggacaac ctggaacctg     2040
ggacctttga tcttgggggg ctatatgaag caattgagga gtgcctgatt aatgatccct     2100 gggtttgct taatgcttct tggttcaact cctccttac acatgcattg agttagttgt     2160
ggcagtgcta ctatttgcta tccatactgt ccaaaa                              2196
```

<210> SEQ ID NO 4
<211> LENGTH: 1532
<212> TYPE: DNA
<213> ORGANISM: Artificial Sequence
<220> FEATURE:
<223> OTHER INFORMATION: DQ874877 (X-31 ca NP)

<400> SEQUENCE: 4

```
gataatcact cactgagtga catcaaaatc atggcgtctc aaggcaccaa acgatcttac       60
gaacagatgg agactgatgg aggacgccag aatgccactg aaatcagagc atccgtcgga      120
aaaatgattg gtggaattgg acgattctac atccaaatgt gcaccgaact caaactcagt      180
```

```
gattatgagg gacggttgat ccaaaacagc ttaacaatag agagaatggt gctctctgct    240
tttgacgaaa ggagaaataa ataccttgaa gaacatccca gtgcggggaa agatcctaag    300
aaaactggag gacctatata caggagagta aacggaaagt ggatgagaga actcatcctt    360
tatgacaaaa agaaaataag gcgaatctgg cgccaagcta ataatggtga cgatgcaatg    420
gctggtctga ctcacatgat gatctggcat tccaatttga atgatgcaac ttatcagagg    480
acaagagctc ttgttcgcac cggaatggat cccaggatgt gctctctgat gcaaggttca    540
actctcccta ggaggtctgg agccgcaggt gctgcagtca aaggagttgg aacaatggtg    600
atggaattgg tcagaatgat caaacgtggg atcaatgatc ggaacttctg gagggggtgag    660 aatggacgaa aaacaagaat tgcttatgaa agaatgtgca acattctcaa agggaaattt    720
caaactgctg cacaaaaagc aatgatggat caagtgagag agagccggaa cccagggaat    780
gctgagttcg aagatctcac ttttctagca cggtctgcac tcatattgag agggtcggtt    840
gctcacaagt cctgcctgcc tgcctgtgtg tatggacctg ccgtagccag tgggtacgac    900
tttgaaaggg agggatactc tctagtcgga atagacccctt tcagactgct tcaaaacagc    960
caagtgtaca gcctaatcag accaaatgag aatccagcac acaagagtca actggtgtgg    1020
atggcatgcc attctgccgc atttgaagat ctaagagtat taagcttcat caagggacg    1080 aaggtgctcc caagagggaa gctttccact agaggagttc aaattgcttc caatgaaaat    1140
atggagacta tggaatcaag tacacttgaa ctgagaagca ggtactgggc cataaggacc    1200
agaagtggag gaaacaccaa tcaacagagg gcatctgcgg gccaaatcag catacaacct    1260
acgttctcag tacagagaaa tctcccttt gacagaacca ccattatggc agcattcaat    1320
gggaatacag aggggagaac atctgacatg aggaccgaaa tcataaggat gatggaaagt    1380
gcaagaccag aagatgtgtc tttccagggg cggggagtct tcgagctctc ggacgaaaag    1440
gcagcgagcc cgatcgtgcc ttcctttgac atgagtaatg aaggatctta tttcttcgga    1500
gacaatgcag aggagtacga caattaaaga aa                                 1532
```

<210> SEQ ID NO 5
<211> LENGTH: 992
<212> TYPE: DNA
<213> ORGANISM: Artificial Sequence
<220> FEATURE:
<223> OTHER INFORMATION: DQ874879 (X-31 ca M)

<400> SEQUENCE: 5

```
attgaaagat gagtcttcta accgaggtcg aaacgtacgt actctctatc atcccgtcag     60
gccccctcaa agccgagatc gcacagagac ttgaagatgt ctttgcaggg aagaacaccg    120
atcttgaggt tctcatggaa tggctaaaga caagaccaat cctgtcacct ctgactaagg    180
ggattttagg atttgtgttc acgctcaccg tgcccagtga gcgaggactg cagcgtagac    240
gctttgtcca aaatgccctt aatgggaacg gggatccaaa taacatggac aaaagcagtta    300 aactgtatag gaagctcaag agggagataa cattccatgg ggccaaagaa atctcactca    360
gttattctgc tggtgcactt gccagttgta tgggcctcat atacaacagg atggggactg    420
tgaccactga gtggcatttg gcctggtat gtgcaacctg tgaacagatt gctgactccc    480
agcatcggtc tcataggcaa atggtgacaa caaccaatcc actaatcaga catgagaaca    540
gaatggtttt agccagcact acagctaagg ctatggagca aatggctgga tcgagtgagc    600
aagcagcaga ggccatggag gttgctagtc aggctagaca aatggtgcaa gcgatgagaa    660
ccattgggac tcatcctagc tccagtgctg gtctgaaaaa tgatcttctt gaaaatttgc    720
```

| | | |
|---|---|---|
| aggcctatca gaaacgaatg ggggtgcaga tgcaacggtt caagtgatcc tctcactatt | 780 | |
| gccgcaaata tcattgggat tttgcacttg acattgtgga ttcttgatcg tctttttttc | 840 | |
| aaatgcattt accgtcgctt taaatacgga ctgaaaggag ggccttctac ggaaggagtg | 900 | |
| ccaaagtcta tgagggaaga atatcgaaag gaacagcaga gtgctgtgga tgctgacgat | 960 | |
| ggtcattttg tcagcataga gctggagtaa aa | 992 | |

<210> SEQ ID NO 6
<211> LENGTH: 852
<212> TYPE: DNA
<213> ORGANISM: Artificial Sequence
<220> FEATURE:
<223> OTHER INFORMATION: DQ874880 (X-31 ca NS)

<400> SEQUENCE: 6

| | | |
|---|---|---|
| aacataatgg atccaaacac tgtgtcaagc tttcaggtag attgctttct ttggcatgtc | 60 | |
| cgcaaacgag ttgcagacca agaactaggt gatgccccat tccttgatcg gcttcgccga | 120 | |
| gatcagaaat ccctaagagg aagggggcagt actctcggtc tggacatcaa gacagccaca | 180 | |
| cgtgctggaa agcagatagt ggagcggatt ctgaaagaag aatccgatga ggcacttaaa | 240 | |
| atgaccatgg cctctgtacc tgcgtcgcgt tacctaactg acatgactct tgaggaattg | 300 | |
| tcaagggact ggtccatgct catacccaag cagaaagtgg caggccctct ttgtatcaga | 360 | |
| atggaccagc gatcatgga taagaacatc atactgaaag cgaacttcag tgtgattttt | 420 | |
| gaccggctgg agactctaat attgctaagg gctttcaccg aagagggagc aattgttggc | 480 | |
| gaaatttcac cattgccttc tcttccagga catactgctg aggatgtcaa aaatgcagtt | 540 | |
| ggagtcctca tcggaggact tgaatggaat gataacacag ttcgagtctc tgaaactcta | 600 | |
| cagagattcg cttggagaag cagtaatgag aatgggagac ctccactcac tccaaaacag | 660 | |
| aaacgagaaa tggcgggaac aattaggtca gaagtttgaa gaaataagat ggttgattga | 720 | |
| agaagtgaga cacaaactga agataacaga gaatagtttt gagcaaataa catttatgca | 780 | |
| agccttacat ctattgcttg aagtggagca agagataaga actttctcgt ttcagcttat | 840 | |
| ttagtactaa aa | 852 | |

<210> SEQ ID NO 7
<211> LENGTH: 1701
<212> TYPE: DNA
<213> ORGANISM: Artificial Sequence
<220> FEATURE:
<223> OTHER INFORMATION: GQ131023 (HA of A/Korea/1/09 (H1N1))

<400> SEQUENCE: 7

| | | |
|---|---|---|
| atgaaggcaa tactagtagt tctgctatat acatttgcaa ccgcaaatgc agacacatta | 60 | |
| tgtataggtt atcatgcgaa caattcaaca gacactgtag acacagtact agaaaagaat | 120 | |
| gtaacagtaa cacactctgt taaccttcta agagacaagc ataacgggaa actatgcaaa | 180 | |
| ctaagagggg tagccccatt gcatttgggt aaatgtaaca ttgctggctg gatcctggga | 240 | |
| aatccagagt gtgaatcact ctccacagca agctcatggt cctacattgt ggaaacatct | 300 | |
| agttcagaca atggaacgtg ttacccagga gatttcatcg attatgagga gctaagagag | 360 | |
| caattgagct cagtgtcatc atttgaaagg tttgagatat tccccaagac aagttcatgg | 420 | |
| cccaatcatg actcgaacaa aggtgtaacg gcagcatgtc ctcatgctgg agcaaaaagc | 480 | |
| ttctacaaaa atttaatatg gctagttaaa aaaggaaatt catacccaaa gctcagcaaa | 540 | |
| tcctacatta atgataagg gaaagaagtc ctcgtgctat ggggcattca ccatccatct | 600 | |

| | |
|---|---:|
| actagtgctg accaacaaag tctctatcag aatgcagatg catatgtttt tgtggggtca | 660 |
| tcaagataca gcaagaagtt caagccggaa atagcaataa gacccaaagt gagggatcaa | 720 |
| gaagggagaa tgaactatta ctggacacta gtagagccgg gagacaaaat aacattcgaa | 780 |
| gcaactggaa atctagtggt accgagatat gcattcgcaa tggaaagaaa tgctggatct | 840 |
| ggtattatca tttcagatac accagtccac gattgcaata caacttgtca gacacccaag | 900 |
| ggtgctataa acaccagcct cccatttcag aatatacatc cgatcacaat ggaaaatgt | 960 |
| ccaaaatatg taaaaagcac aaaattgaga ctggccacag gattgaggaa tgtcccgtct | 1020 |
| attcaatcta gaggcctatt tggggccatt gccggtttca ttgaagggg gtggacaggg | 1080 |
| atggtagatg gatggtacgg ttatcaccat caaaatgagc aggggtcagg atatgcagcc | 1140 |
| gacctgaaga gcacacagaa tgccattgac gagattacta acaaagtaaa ttctgttatt | 1200 |
| gaaagatga atacacagtt cacagcagta ggtaaagagt caaccacct ggaaaaaaga | 1260 |
| atagagaatt taaataaaaa agttgatgat ggtttcctgg acatttggac ttacaatgcc | 1320 |
| gaactgttgg ttctattgga aaatgaaaga actttggact accacgattc aaatgtgaag | 1380 |
| aacttatatg aaaaggtaag aagccagcta aaaacaatg ccaaggaaat tggaaacggc | 1440 |
| tgctttgaat tttaccacaa atgcgataac acgtgcatgg aaagtgtcaa aaatgggact | 1500 |
| tatgactacc caaaatactc agaggaagca aaattaaaca gagaagaaat agatggggta | 1560 |
| aagctggaat caacaaggat ttaccagatt ttggcgatct attcaactgt cgccagttca | 1620 |
| ttggtactgg tagtctccct gggggcaatc agtttctgga tgtgctctaa tgggtctcta | 1680 |
| cagtgtagga tatgtattta a | 1701 |

<210> SEQ ID NO 8
<211> LENGTH: 1410
<212> TYPE: DNA
<213> ORGANISM: Artificial Sequence
<220> FEATURE:
<223> OTHER INFORMATION: GQ132185 (NA of A/Korea/1/09 (H1N1))

<400> SEQUENCE: 8

| | |
|---|---:|
| atgaatccaa accaaaagat aataaccatt ggttcggtct gtatgacaat tggaatggct | 60 |
| aacttaatat tacaaattgg aaacataatc tcaatatgga ttagccactc aattcaactt | 120 |
| gggaatcaaa atcagattga acatgcaat caaagcgtca ttacttatga aaacaacact | 180 |
| tgggtaaatc agacatatgt taacatcagc aacaccaact tgctgctgg acagtcagtg | 240 |
| gtttccgtga aattagcggg caattcctct ctctgccctg ttagtggatg gctatatac | 300 |
| agtaaagaca acagtataag aatcggttcc aagggggatg tgtttgtcat aagggaacca | 360 |
| ttcatatcat gctccccctt ggaatgcaga accttcttct tgactcaagg ggccttgcta | 420 |
| aatgacaaac attccaatgg aaccattaaa gacaggagcc catatcgaac cctaatgagc | 480 |
| tgtcctattg gtgaagttcc ctctccatac aactcaagat tgagtcagt cgcttggtca | 540 |
| gcaagtgctt gtcatgatgg catcaattgg ctaacaattg gaatttctgg cccagacaat | 600 |
| ggggcagtgg ctgtgttaaa gtacaacgga ataataacag acactatcaa gagttggaga | 660 |
| aacaatatat tgagaacaca gagtctgaa tgtgcatgtg taaatggttc ttgctttact | 720 |
| gtaatgaccg atggaccaag taatggacag gcctcataca agatcttcag aatagaaaag | 780 |
| ggaaagatag tcaaatcagt cgaaatgaat gcccctaatt atcactatga ggaatgctcc | 840 |
| tgttatcctg attctagtga aatcacatgt gtgtgcaggg ataactggca tggctcgaat | 900 |
| cgaccgtggg tgtctttcaa ccagaatctg gaatatcaga taggatacat atgccgtggg | 960 |

```
attttcggag acaatccacg ccctaatgat aagacaggca gttgtggtcc agtatcgtct    1020
aatggagcaa atggagtaaa aggattttca ttcaaatacg gcaatggtgt ttggataggg    1080
agaactaaaa gcattagttc aagaaacggt tttgagatga tttgggatcc gaacggatgg    1140
actgggacac acaataactt ctcaataaag caagatatcg taggaataaa tgagtggtca    1200
ggatatagcg ggagttttgt tcagcatcca gaactaacag ggctggattg tataagacct    1260
tgcttctggg ttgaactaat cagagggcga cccaaagaga acacaatctg gactagcggg    1320
agcagcatat cctttttgtgg tgtaaacagt gacactgtgg gttggtcttg gccagacggt    1380
gctgagttgc catttaccat tgacaagtaa                                     1410

<210> SEQ ID NO 9
<211> LENGTH: 1775
<212> TYPE: DNA
<213> ORGANISM: Artificial Sequence
<220> FEATURE:
<223> OTHER INFORMATION: CY031336 (HA of A/New Caledonia/20/99 (H1N1))

<400> SEQUENCE: 9
agcaaaagca gggaaaaata aaaacaacca aaatgaaagc aaaactactg gtcctgttat      60
gtacatttac agctacatat gcagacacaa tatgtatagg ctaccatgcc aacaactcaa     120
ccgacactgt tgacacagta cttgagaaga atgtgacagt gacacactct gtcaacctac     180
ttgaggacag tcacaatgga aaactatgtc tactaaaagg aatagcccca ctacaattgg     240
gtaattgcag cgttgccgga tggatcttag gaaacccaga atgcgaatta ctgatttcca     300
aggaatcatg gtcctacatt gtagaaacac caatcctga gaatgaaca tgttacccag     360 ggtatttcgc cgactatgag gaactgaggg agcaattgag ttcagtatct tcatttgaga     420
gattcgaaat attccccaaa gaaagctcat ggcccaccca caccgtaacc ggagtatcag     480
catcatgctc ccataatggg aaaagcagtt tttacagaaa tttgctatgg ctgacgggga     540
agaatggttt gtacccaaac ctgagcaagt cctatgtaaa caacaaagag aaagaagtcc     600
ttgtactatg gggtgttcat cacccgccta acataggga ccaaggggcc ctctatcata     660
cagaaaatgc ttatgtctct gtagtgtctt cacattatag cagaagattc accccagaaa     720
tagccaaaag acccaaagta agagatcagg aaggaagaat caactactac tggactctgc     780
tggaacctgg ggatacaata atatttgagg caaatggaaa tctaatagcg ccatggtatg     840
cttttgcact gagtagaggc tttggatcag gaatcatcac ctcaaatgca ccaatggatg     900
aatgtgatgc gaagtgtcaa acacctcagg agctataaa cagcagtctt ctttccaga     960 atgtacaccc agtcacaata ggagagtgtc caaagtatgt caggagtgca aaattaagga    1020
tggttacagg actaaggaac atcccatcca ttcaatccag aggtttgttt ggagccattg    1080
ccggtttcat tgaagggggg tggactggaa tggtagatgg gtggtatggt tatcatcatc    1140
agaatgagca aggatctggc tatgctgcag atcaaaaaag tacacaaaat gccattaacg    1200
ggattacaaa caaggtgaat tctgtaattg agaaatgaa cactcaattc acagctgtgg    1260
gcaaagaatt caacaaattg gaaagaagga tggaaaactt aaataaaaaa gttgatgatg    1320
ggtttctaga catttggaca tataatgcag aattgttggt tctactggaa atgaaagga    1380 ctttggattt ccatgactcc aatgtgaaga atctgtatga gaaagtaaaaa agccaattaa    1440 agaataatgc caaagaaata ggaaacgggt gttttgaatt ctatcacaag tgtaacaatg    1500
aatgcatgga gagtgtgaaa atggaacttaa tgactatcc aaaatattcc gaagaatcaa    1560
agttaaacag ggagaaaatt gatggagtga aattggaatc aatgggagtc tatcagattc    1620
```

-continued tggcgatcta ctcaactgtc gccagttccc tggttctttt ggtctccctg ggggcaatca 1680
gcttctggat gtgttccaat gggtctttgc agtgtagaat atgcatctga gaccagaatt 1740
tcagaaatat aagaaaaaac acccttgttt ctact 1775

<210> SEQ ID NO 10
<211> LENGTH: 1414
<212> TYPE: DNA
<213> ORGANISM: Artificial Sequence
<220> FEATURE:
<223> OTHER INFORMATION: CY033624 (NA of A/New Caledonia/20/99 (H1N1))

<400> SEQUENCE: 10
aatgaatcca aatcaaaaaa taataaccat tggatcaatc agtatagcaa tcggaataat 60
tagtctaatg ttgcaaatag gaaatattat ttcaatatgg gctagtcact caatccaaac 120
tggaagtcaa aaccacactg gagtatgcaa ccaaagaatc atcacatatg aaaacagcac 180
ctgggtgaat cacacatatg ttaatattaa caacactaat gttgttgctg gaaaggacaa 240
aacttcagtg acattggccg gcaattcatc tctttgttct atcagtggat gggctatata 300
cacaaaagac aacagcataa gaattggctc caaaggagat gtttttgtca taagagaacc 360
tttcatatca tgttctcact tggaatgcag aacctttttt ctgacccaag gtgctctatt 420
aaatgacaaa cattcaaatg ggaccgttaa ggacagaagt ccttataggg ccttaatgag 480
ctgtcctcta ggtgaagctc cgtccccata caattcaaag tttgaatcag ttgcatggtc 540
agcaagcgca tgccatgatg gcatgggctg gttaacaatc ggaatttctg gtccagacaa 600
tggagctgtg gctgtactaa aatacaacgg cataataact gaaaccataa aaagttggaa 660
aaagcgaata ttaagaacac aagagtctga atgtgtctgt gtgaacgggt catgtttcac 720
cataatgacc gatggcccga gtaatggggc cgcctcgtac aaaatcttca agatcgaaaa 780
ggggaaggtt actaaatcaa tagagttgaa tgcacccaat tttcattatg aggaatgttc 840
ctgttaccca gacactggca cagtgatgtg tgtatgcagg gacaactggc atggttcaaa 900
tcgaccttgg gtgtctttta atcaaaacct ggattatcaa ataggataca tctgcagtgg 960
ggtgttcggt gacaatccgc gtcccaaaga tggagagggc agctgtaatc cagtgactgt 1020
tgatggagca gacggagtaa aggggttttc atacaaatat ggtaatggtg tttggatagg 1080
aaggactaaa agtaacagac ttagaaaggg gtttgagatg atttgggatc ctaatggatg 1140
gacagatacc gacagtgatt tctcagtgaa acaggatgtt gtggcaataa ctgattggtc 1200
agggtacagc ggaagtttcg ttcaacatcc tgagttaaca ggattggact gtataagacc 1260
ttgcttctgg gttgagttag tcagaggact gcctagagaa aatacaacaa tctggactag 1320
tgggagcagc atttcttttt gtggcgtaaa tagtgatact gcaaactggt cttggccaga 1380
cggtgctgag ttgccgttca ccattgacaa gtag 1414

<210> SEQ ID NO 11
<211> LENGTH: 1779
<212> TYPE: DNA
<213> ORGANISM: Artificial Sequence
<220> FEATURE:
<223> OTHER INFORMATION: CY116646 (HA of A/Indonesia/5/05 (H5N1))

<400> SEQUENCE: 11
agcaaaagca ggggttcaat ctgtaaaaat ggagaaaata gtgcttcttc ttgcaatagt 60
cagtcttgtt aaaagtgatc agatttgcat tggttaccat gcaaacaatt caacagagca 120
ggttgacaca atcatggaaa agaacgttac tgttacacat gcccaagaca tactggaaaa 180

| | | | |
|---|---|---|---|
| gacacacaac | gggaagctct | gcgatctaga | tggagtgaag | cctctaattt | taagagattg | 240 |
| tagtgtagct | ggatggctcc | tcgggaaccc | aatgtgtgac | gaattcatca | atgtaccgga | 300 |
| atggtcttac | atagtggaga | aggccaatcc | aaccaatgac | ctctgttacc | cagggagttt | 360 |
| caacgactat | gaagaactga | acacctatt | gagcagaata | aaccattttg | agaaaattca | 420 |
| aatcatcccc | aaaagttctt | ggtccgatca | tgaagcctca | tcaggagtga | gctcagcatg | 480 |
| tccatacctg | ggaagtccct | cctttttag | aaatgtggta | tggcttatca | aaagaacag | 540 |
| tacataccca | acaataaaga | aaagctacaa | taataccaac | caagaagatc | ttttggtact | 600 |
| gtggggaatt | caccatccta | atgatgcggc | agagcagaca | aggctatatc | aaacccaac | 660 |
| cacctatatt | tccattggga | catcaacact | aaaccagaga | ttggtaccaa | aaatagctac | 720 |
| tagatccaaa | gtaaacgggc | aaagtggaag | gatggagttc | ttctggacaa | ttttaaaacc | 780 |
| taatgatgca | atcaacttcg | agagtaatgg | aaatttcatt | gctccagaat | atgcatacaa | 840 |
| aattgtcaag | aaagggggact | cagcaattat | gaaaagtgaa | ttggaatatg | gtaactgcaa | 900 |
| caccaagtgt | caaactccaa | tgggggcgat | aaactctagt | atgccattcc | acaacataca | 960 |
| ccctctcacc | atcggggaat | gccccaaata | tgtgaaatca | aacagattag | tccttgcaac | 1020 |
| agggctcaga | atagccctc | aaagagagag | cagaagaaaa | aagagaggac | tatttggagc | 1080 |
| tatagcaggt | tttatagagg | gaggatggca | gggaatggta | gatggttggt | atgggtacca | 1140 |
| ccatagcaat | gagcagggga | gtgggtacgc | tgcagacaaa | gaatccactc | aaaaggcaat | 1200 |
| agatggagtc | accaataaag | tcaactcaat | cattgacaaa | atgaacactc | agtttgaggc | 1260 |
| cgttggaagg | gaatttaata | acttagaaag | gagaatagaa | aatttaaaca | agaagatgga | 1320 |
| agacgggttt | ctagatgtct | ggacttataa | tgccgaactt | ctggttctca | tggaaaatga | 1380 |
| gagaactcta | gactttcatg | actcaaatgt | taagaacctc | tacgacaagg | tccgactaca | 1440 |
| gcttagggat | aatgcaaagg | agctgggtaa | cggttgtttc | gagttctatc | acaaatgtga | 1500 |
| taatgaatgt | atggaaagta | taagaaacgg | aacgtacaac | tatccgcagt | attcagaaga | 1560 |
| agcaagatta | aaaagagagg | aaataagtgg | ggtaaaattg | gaatcaatag | gaacttacca | 1620 |
| aatactgtca | atttattcaa | cagtggcgag | ttccctagca | ctggcaatca | tgatggctgg | 1680 |
| tctatcttta | tggatgtgct | ccaatggatc | gttacaatgc | agaatttgca | tttaaatttg | 1740 |
| tgagttcaga | ttgtagttaa | aaacaccctt | gtttctact | | | 1779 |

<210> SEQ ID NO 12
<211> LENGTH: 1398
<212> TYPE: DNA
<213> ORGANISM: Artificial Sequence
<220> FEATURE:
<223> OTHER INFORMATION: CY116648 (NA of A/Indonesia/5/05 (H5N1))

<400> SEQUENCE: 12

| | | | |
|---|---|---|---|
| agcaaaagca | ggagttcaaa | atgaatccaa | atcagaagat | aataaccatt | ggatcaatct | 60 |
| gtatggtaat | tggaatagtt | agcttaatgt | tacaaattgg | gaacatgatc | tcaatatggg | 120 |
| tcattcattc | aattcagaca | gggaatcaac | accaagctga | atcaatcagc | aatactaacc | 180 |
| ctcttactga | gaaagctgtg | gcttcagtaa | cattagcggg | caattcatct | ctttgccca | 240 |
| ttagaggatg | ggctgtacac | agtaaggaca | acaatataag | gatcggttcc | aagggggatg | 300 |
| tgtttgttat | tagagagccg | ttcatctcat | gctcccacct | ggaatgcaga | actttcttct | 360 |
| tgactcaggg | agccttgctg | aatgacaagc | actccaacgg | gactgtcaaa | gacagaagcc | 420 |
| ctcacagaac | attaatgagt | tgtcctgtgg | ggaggctcc | ctctccatat | aactcaaggt | 480 |

```
ttgagtctgt tgcttggtca gcaagtgctt gccatgatgg caccagttgg ttgacaattg      540
gaatttctgg cccagacaat gaggctgtgg ctgtattgaa atacaatggc ataataacag      600
acactatcaa gagttggagg aacgacatac tgagaactca agagtctgaa tgtgcatgtg      660
taaatggctc ttgctttact gtaatgactg atggaccaag taatgggcag gcatcatata      720
agatcttcaa aatggaaaaa ggaaaagtgg tcaaatcagt cgaattggat gctcctaatt      780
atcactatga ggaatgctcc tgttatcctg atgccggcga aatcacatgt gtttgcaggg      840
ataattggca tggctcaaat aggccatggg tatctttcaa tcaaaatttg gagtatcaaa      900
taggatatat atgcagtgga gttttcggag acaatccacg ccccaatgat ggaacaggta      960
gttgtggccc gatgtcccct aacggggcat atggggtaaa agggttttca tttaaatacg     1020
gcaatggtgt ttggatcggg agaaccaaaa gcactaattc caggagcggc tttgaaatga     1080
tttgggatcc aaatgggtgg actggaacgg acagtagctt ttcagtgaaa caagatatag     1140
tagcaataac tgattggtca ggatatagcg ggagttttgt ccagcatcca gaactgacag     1200
gattagattg cataagacct tgtttctggg ttgagttaat cagagggcgg cccaaagaga     1260
gcacaatttg gactagtggg agcagcatat ctttttgtgg tgtaaatagt gacactgtga     1320
gttggtcttg gccagacggt gctgagttgc cattcaccat tgacaagtag tttgttcaaa     1380
aaactccttg tttctact                                                   1398
```